US008945232B2

(12) United States Patent
Sander et al.

(10) Patent No.: US 8,945,232 B2
(45) Date of Patent: Feb. 3, 2015

(54) BALL AND SOCKET IMPLANTS FOR CORRECTION OF HAMMER TOES AND CLAW TOES

(71) Applicants: Elizabeth Sander, Memphis, TN (US); Christine M. Petteys, Bartlett, TN (US); Brian Thoren, Memphis, TN (US)

(72) Inventors: Elizabeth Sander, Memphis, TN (US); Christine M. Petteys, Bartlett, TN (US); Brian Thoren, Memphis, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 90 days.

(21) Appl. No.: 13/839,573

(22) Filed: Mar. 15, 2013

(65) Prior Publication Data

US 2014/0188238 A1   Jul. 3, 2014

Related U.S. Application Data

(60) Provisional application No. 61/747,429, filed on Dec. 31, 2012.

(51) Int. Cl.
*A61F 2/42* (2006.01)
*A61F 2/30* (2006.01)

(52) U.S. Cl.
CPC ............. *A61F 2/4225* (2013.01); *A61F 2/4241* (2013.01); *A61F 2002/30062* (2013.01); *A61F 2002/30607* (2013.01); *A61F 2002/30649* (2013.01); *A61F 2002/30662* (2013.01); *A61F 2002/30672* (2013.01); *A61F 2002/4248* (2013.01); *A61F 2002/4251* (2013.01)
USPC ................... 623/21.19; 623/18.11; 623/21.15

(58) Field of Classification Search
CPC .. A61F 2/4225; A61F 2002/4233; A61F 2/38
USPC ........... 623/11.11, 16.11, 18.11, 21.16–21.19
See application file for complete search history.

(56) References Cited

U.S. PATENT DOCUMENTS

| 348,589 | A | 9/1886 | Sloan |
|---|---|---|---|
| 373,074 | A | 11/1887 | Jones |
| 430,236 | A | 6/1890 | Rogers |
| 561,968 | A | 6/1896 | Coulon |
| 821,025 | A | 5/1906 | Davies |
| 1,966,835 | A | 7/1934 | Stites |
| 2,140,749 | A | 12/1938 | Kaplan |
| 2,361,107 | A | 10/1944 | Johnson |
| 2,600,517 | A | 6/1952 | Rushing |
| 2,895,368 | A | 7/1959 | Place |

(Continued)

FOREIGN PATENT DOCUMENTS

| EP | 0340159 A1 | 11/1989 |
|---|---|---|
| EP | 0409364 A2 | 1/1991 |

(Continued)

OTHER PUBLICATIONS

European Search Report for Application No. EP 13 19 9832 dated Mar. 25, 2014.

*Primary Examiner* — Jason-Dennis Stewart
(74) *Attorney, Agent, or Firm* — Duane Morris LLP

(57) ABSTRACT

A toe bone implant for correction of toe bone deformities is provided. The toe bone implant includes a first portion having a socket portion. The toe bone implant also includes a second portion having a ball portion operatively connected to the socket portion. The toe bone implant is implanted in a joint such that the ball portion is configured to rotate a predetermined amount respective to the socket portion.

18 Claims, 20 Drawing Sheets

(56) References Cited

U.S. PATENT DOCUMENTS

| | | | |
|---|---|---|---|
| 3,466,669 A | 9/1969 | Flatt | |
| 3,681,786 A | 8/1972 | Lynch | |
| 4,156,296 A | 5/1979 | Johnson et al. | |
| 4,204,284 A | 5/1980 | Koeneman | |
| 4,213,208 A | 7/1980 | Marne | |
| 4,262,665 A | 4/1981 | Roalstad et al. | |
| 4,275,717 A | 6/1981 | Bolesky | |
| 4,276,660 A | 7/1981 | Laure | |
| 4,304,011 A | 12/1981 | Whelan, III | |
| 4,367,562 A | 1/1983 | Gauthier | |
| 4,516,569 A | 5/1985 | Evans et al. | |
| 4,590,928 A | 5/1986 | Hunt et al. | |
| 4,642,122 A | 2/1987 | Steffee | |
| 4,655,661 A | 4/1987 | Brandt | |
| 4,731,087 A | 3/1988 | Sculco et al. | |
| 4,865,606 A | 9/1989 | Rehder | |
| 4,908,031 A | 3/1990 | Frisch | |
| 4,915,092 A | 4/1990 | Firica et al. | |
| 4,932,974 A | 6/1990 | Pappas et al. | |
| 4,955,916 A | 9/1990 | Carignan et al. | |
| 4,963,144 A | 10/1990 | Huene | |
| 4,969,909 A | 11/1990 | Barouk | |
| 5,007,932 A | 4/1991 | Bekki et al. | |
| 5,011,497 A | 4/1991 | Persson et al. | |
| 5,037,440 A | 8/1991 | Koenig | |
| 5,047,059 A | 9/1991 | Saffar | |
| 5,062,851 A | 11/1991 | Branemark | |
| 5,092,896 A | 3/1992 | Meuli et al. | |
| 5,133,761 A | 7/1992 | Krouskop | |
| 5,171,252 A | 12/1992 | Friedland | |
| 5,179,915 A | 1/1993 | Cohen et al. | |
| 5,199,839 A | 4/1993 | DeHaitre | |
| 5,207,712 A * | 5/1993 | Cohen | 623/21.19 |
| 5,246,443 A | 9/1993 | Mai | |
| 5,326,366 A | 7/1994 | Pascarella et al. | |
| 5,330,476 A | 7/1994 | Hiot et al. | |
| 5,354,301 A | 10/1994 | Castellano | |
| 5,358,405 A | 10/1994 | Imai | |
| 5,360,450 A | 11/1994 | Giannini | |
| 5,380,334 A | 1/1995 | Torrie et al. | |
| 5,417,692 A | 5/1995 | Goble et al. | |
| 5,425,776 A | 6/1995 | Cohen | |
| 5,425,777 A | 6/1995 | Sarkisian et al. | |
| 5,437,674 A | 8/1995 | Worcel et al. | |
| 5,458,648 A | 10/1995 | Berman et al. | |
| 5,470,230 A | 11/1995 | Daftary et al. | |
| 5,480,447 A | 1/1996 | Skiba | |
| 5,484,443 A | 1/1996 | Pascarella et al. | |
| 5,498,265 A | 3/1996 | Asnis et al. | |
| 5,516,248 A | 5/1996 | DeHaitre | |
| 5,522,903 A | 6/1996 | Sokolow et al. | |
| 5,529,075 A | 6/1996 | Clark | |
| 5,591,165 A | 1/1997 | Jackson | |
| 5,595,563 A | 1/1997 | Moisdon | |
| 5,601,558 A | 2/1997 | Torrie et al. | |
| 5,634,925 A | 6/1997 | Urbanski | |
| 5,669,913 A | 9/1997 | Zobel | |
| 5,674,297 A | 10/1997 | Lane et al. | |
| 5,683,466 A | 11/1997 | Vitale | |
| 5,707,395 A | 1/1998 | Li | |
| 5,713,904 A | 2/1998 | Errico et al. | |
| 5,725,585 A | 3/1998 | Zobel | |
| 5,776,202 A | 7/1998 | Copf et al. | |
| 5,779,707 A | 7/1998 | Bertholet et al. | |
| 5,919,193 A | 7/1999 | Slavitt | |
| 5,951,288 A | 9/1999 | Sawa | |
| 5,984,971 A | 11/1999 | Faccioli et al. | |
| 6,030,162 A | 2/2000 | Huebner | |
| 6,045,573 A | 4/2000 | Wenstrom, Jr. et al. | |
| 6,048,343 A | 4/2000 | Mathis et al. | |
| 6,099,571 A | 8/2000 | Knapp | |
| 6,200,321 B1 | 3/2001 | Orbay et al. | |
| 6,200,345 B1 | 3/2001 | Morgan | |
| 6,224,600 B1 | 5/2001 | Protogirou | |
| 6,248,109 B1 | 6/2001 | Stofella | |
| 6,319,284 B1 | 11/2001 | Rushdy et al. | |
| 6,332,885 B1 | 12/2001 | Martella | |
| 6,336,928 B1 | 1/2002 | Guerin et al. | |
| 6,352,560 B1 | 3/2002 | Poeschmann et al. | |
| 6,383,223 B1 | 5/2002 | Baehler et al. | |
| 6,386,877 B1 | 5/2002 | Sutter | |
| 6,413,260 B1 | 7/2002 | Berrevoets et al. | |
| 6,423,097 B2 | 7/2002 | Rauscher | |
| 6,454,808 B1 | 9/2002 | Masada | |
| 6,458,134 B1 | 10/2002 | Songer et al. | |
| 6,475,242 B1 * | 11/2002 | Bramlet | 623/21.11 |
| 6,508,841 B2 | 1/2003 | Martin et al. | |
| 6,517,543 B1 | 2/2003 | Berrevoets et al. | |
| 6,533,788 B1 | 3/2003 | Orbay | |
| 6,551,343 B1 | 4/2003 | Törmälä et al. | |
| 6,575,976 B2 | 6/2003 | Grafton | |
| 6,682,565 B1 * | 1/2004 | Krishnan | 623/21.16 |
| 6,875,235 B2 | 4/2005 | Ferree | |
| 7,037,309 B2 | 5/2006 | Weil et al. | |
| 7,041,106 B1 | 5/2006 | Carver et al. | |
| 7,192,445 B2 | 3/2007 | Ellingsen et al. | |
| 7,207,994 B2 | 4/2007 | Vlahos et al. | |
| 7,291,175 B1 | 11/2007 | Gordon | |
| 7,585,316 B2 | 9/2009 | Trieu | |
| 7,588,603 B2 | 9/2009 | Leonard | |
| 7,695,471 B2 | 4/2010 | Cheung et al. | |
| 7,708,759 B2 | 5/2010 | Lubbers et al. | |
| 7,727,235 B2 | 6/2010 | Contiliano et al. | |
| 7,837,738 B2 | 11/2010 | Reigstad et al. | |
| 7,887,589 B2 | 2/2011 | Glenn et al. | |
| 7,909,880 B1 | 3/2011 | Grant | |
| 7,918,879 B2 | 4/2011 | Yeung et al. | |
| 7,959,681 B2 | 6/2011 | Lavi | |
| 8,002,811 B2 | 8/2011 | Corradi et al. | |
| 8,100,983 B2 | 1/2012 | Schulte | |
| 8,118,839 B2 | 2/2012 | Taylor | |
| 8,118,849 B2 | 2/2012 | Wahl et al. | |
| 8,197,509 B2 | 6/2012 | Contiliano et al. | |
| 8,262,712 B2 | 9/2012 | Coilard-Lavirotte et al. | |
| 8,394,132 B2 | 3/2013 | Lewis et al. | |
| 8,414,583 B2 | 4/2013 | Prandi et al. | |
| 2001/0049529 A1 | 12/2001 | Cachia et al. | |
| 2002/0072803 A1 | 6/2002 | Saunders et al. | |
| 2002/0111690 A1 | 8/2002 | Hyde | |
| 2003/0191422 A1 | 10/2003 | Sossong | |
| 2004/0097941 A1 | 5/2004 | Weiner et al. | |
| 2004/0220574 A1 | 11/2004 | Pelo et al. | |
| 2004/0230313 A1 | 11/2004 | Saunders | |
| 2005/0123672 A1 | 6/2005 | Justin et al. | |
| 2005/0149031 A1 | 7/2005 | Ciccone et al. | |
| 2005/0187636 A1 | 8/2005 | Graham | |
| 2005/0283159 A1 | 12/2005 | Amara | |
| 2006/0074492 A1 | 4/2006 | Frey | |
| 2006/0100715 A1 | 5/2006 | De Villiers | |
| 2006/0129153 A1 | 6/2006 | Klaue et al. | |
| 2006/0200151 A1 | 9/2006 | Ducharme et al. | |
| 2006/0247787 A1 | 11/2006 | Rydell et al. | |
| 2007/0078518 A1 | 4/2007 | Lavi | |
| 2007/0142920 A1 | 6/2007 | Niemi | |
| 2007/0185583 A1 | 8/2007 | Branemark | |
| 2007/0213831 A1 | 9/2007 | de Cubber | |
| 2008/0051912 A1 | 2/2008 | Hollawell | |
| 2008/0086139 A1 | 4/2008 | Bourke et al. | |
| 2008/0132894 A1 | 6/2008 | Coilard-Lavirotte et al. | |
| 2008/0132958 A1 | 6/2008 | Pech et al. | |
| 2008/0161919 A1 | 7/2008 | Melkent | |
| 2008/0177262 A1 | 7/2008 | Augoyard et al. | |
| 2008/0177334 A1 | 7/2008 | Stinnette | |
| 2008/0195215 A1 | 8/2008 | Morton | |
| 2008/0221697 A1 | 9/2008 | Graser | |
| 2008/0255618 A1 | 10/2008 | Fisher et al. | |
| 2009/0036893 A1 | 2/2009 | Kartalian et al. | |
| 2010/0131014 A1 | 5/2010 | Peyrot et al. | |
| 2010/0131072 A1 | 5/2010 | Schulte | |
| 2010/0185295 A1 | 7/2010 | Emmanuel | |
| 2010/0249942 A1 | 9/2010 | Goswami et al. | |
| 2010/0262254 A1 | 10/2010 | Lawrence et al. | |
| 2010/0274293 A1 | 10/2010 | Terrill et al. | |
| 2011/0004255 A1 | 1/2011 | Weiner et al. | |

(56) References Cited

U.S. PATENT DOCUMENTS

| | | |
|---|---|---|
| 2011/0082507 A1 | 4/2011 | Slaue |
| 2011/0082508 A1 | 4/2011 | Reed |
| 2011/0093017 A1 | 4/2011 | Prasad et al. |
| 2011/0093085 A1 | 4/2011 | Morton |
| 2011/0144644 A1 | 6/2011 | Prandi et al. |
| 2011/0257652 A1 | 10/2011 | Roman |
| 2011/0301652 A1 | 12/2011 | Reed et al. |
| 2011/0301653 A1 | 12/2011 | Reed et al. |
| 2012/0016428 A1 | 1/2012 | White et al. |
| 2012/0065692 A1 | 3/2012 | Champagne et al. |
| 2012/0089197 A1 | 4/2012 | Anderson |
| 2012/0259419 A1 | 10/2012 | Brown et al. |
| 2013/0030475 A1 | 1/2013 | Weiner et al. |
| 2013/0053975 A1 | 2/2013 | Reed et al. |
| 2013/0060295 A1 | 3/2013 | Reed et al. |
| 2013/0066383 A1 | 3/2013 | Anderson et al. |
| 2013/0066435 A1 | 3/2013 | Averous et al. |
| 2013/0079776 A1 | 3/2013 | Zwirkoski et al. |
| 2013/0131822 A1 | 5/2013 | Lewis et al. |
| 2013/0150965 A1 | 6/2013 | Taylor et al. |

FOREIGN PATENT DOCUMENTS

| | | |
|---|---|---|
| EP | 0551846 A1 | 7/1993 |
| EP | 0611557 A3 | 8/1994 |
| EP | 0738502 A2 | 10/1996 |
| EP | 1708653 B1 | 9/2009 |
| EP | 1923012 B1 | 6/2010 |
| EP | 1868536 B1 | 11/2010 |
| EP | 2275055 B1 | 5/2012 |
| EP | 2221025 B1 | 12/2012 |
| EP | 2221026 B1 | 3/2013 |
| FR | 736058 | 11/1932 |
| FR | 1036978 | 9/1953 |
| FR | 2605878 A1 | 5/1988 |
| FR | 2645735 A1 | 10/1990 |
| FR | 2651119 A1 | 3/1991 |
| FR | 2783702 A1 | 3/2000 |
| FR | 2787313 A1 | 6/2000 |
| FR | 2794019 A1 | 12/2000 |
| FR | 2846545 A1 | 5/2004 |
| GB | 140983 | 4/1920 |
| GB | 2119655 A | 11/1983 |
| GB | 2227540 A | 8/1990 |
| GB | 2336415 A | 10/1999 |
| GB | 2430625 A | 4/2007 |
| WO | 96/41596 A1 | 12/1996 |
| WO | 98/47449 A1 | 10/1998 |
| WO | 2005094706 A1 | 10/2005 |
| WO | 2006109004 A1 | 10/2006 |
| WO | 2007135322 A1 | 11/2007 |

\* cited by examiner

BALL AND SOCKET IMPLANTS FOR CORRECTION OF HAMMER TOES AND CLAW TOES

CROSS REFERENCES

The present application is co-pending with and claims the priority benefit of the provisional application entitled, "Ball and Socket Implants for Correction of Hammer Toes and Claw Toes" Application Ser. No. 61/747,429, filed on Dec. 31, 2012, the entirety of which is incorporated herein by reference.

FIELD

The disclosed devices and methods generally relates to hammer toe and claw toe correction implants and devices.

BACKGROUND

A hammer toe or contracted toe is a deformity of the proximal inter-phalangeal joint of the second, third, or fourth toe causing it to be permanently bent and giving it a semblance of a hammer. Initially, the hammer toes are flexible and may be corrected with simple measures but, if left untreated, they get fixed and require surgical intervention for correcting them. People with hammer toe can have corns or calluses on the top of the middle joint of the toe or on the tip of the toe. They can also feel pain in their toes or feet and have difficulty in finding comfortable shoes. A claw toe is a typically a deformity of the metatarsal phalangeal joint of the second, third, fourth, or fifth toe causing unopposed flexion of the proximal inter-phalangeal joint and distal inter-phalangeal joint in the respective toe and giving it a semblance of a claw.

Various treatment strategies are available for correcting hammer toes and claw toes. First line treatment of hammer toes starts with new shoes that have soft and spacious toe boxes. Some toe exercises may also be prescribed, to stretch and strengthen the muscles. For example, gently stretching the toes manually, using the toes to pick up things off the floor etc. Another line of treatment includes using straps, cushions or non-medicated corn pads to relieve symptoms. Further, a hammer toe or claw toe can be corrected by a surgery if the other treatment options fail. Surgery can involve inserting screws, wires etc. or other similar implants in toes to straighten them.

Traditional surgical methods include use of k-wires. But of late, due to various disadvantages of using K-wires, compression screws are being used as an implant. K-wires require pings protruding through end of toes because they are temporarily inserted. Because of this, k-wires lead to pin tract infections, loss of fixation etc. Other disadvantages of k-wires include migration of k-wires and breakage, and may therefore require multiple surgeries.

Accordingly, there remains a need for developing improved toe bone implants and methods of correcting toe bone deformities.

BRIEF DESCRIPTION OF THE DRAWINGS

Various aspects of the present disclosure will be or become apparent to one with skill in the art by reference to the following detailed description when considered in connection with the accompanying exemplary non-limiting embodiments.

DETAILED DESCRIPTION

Figure 1A:
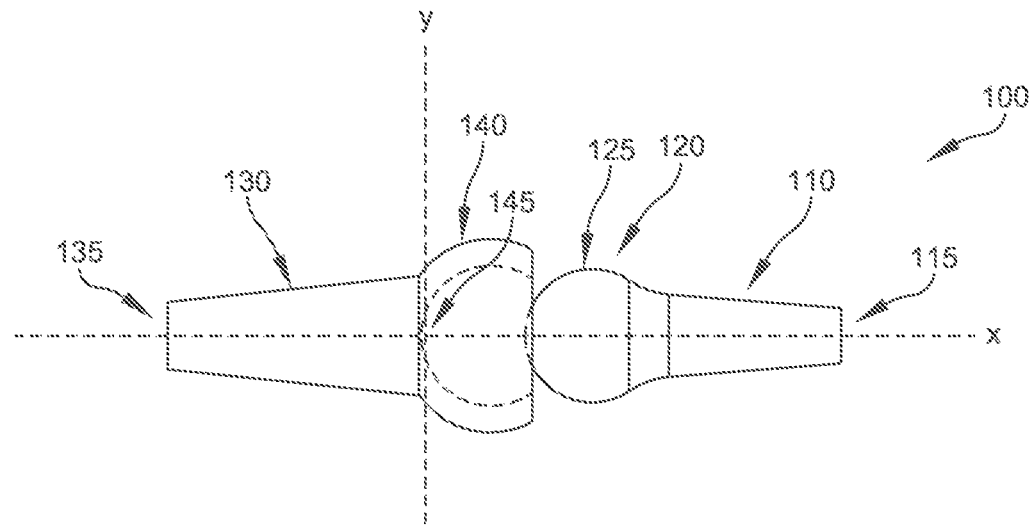
FIG. 1A is a side elevational view, partially in phantom, of a hammertoe implant formed in accordance with one embodiment of the invention.

With reference to the Figures, where like elements have been given like numerical designations to facilitate an understanding of the drawings, the various embodiments of cyclic deposition and etch methods are described. The figures are not drawn to scale.

The following description is provided as an enabling teaching of a representative set of examples. Many changes can be made to the embodiments described herein while still obtaining beneficial results. Some of the desired benefits discussed below can be obtained by selecting some of the features or steps discussed herein without utilizing other features or steps. Accordingly, many modifications and adaptations, as well as subsets of the features and steps described herein are possible and can even be desirable in certain circumstances. Thus, the following description is provided as illustrative and is not limiting.

This description of illustrative embodiments is intended to be read in connection with the accompanying drawings, which are to be considered part of the entire written description. In the description of embodiments disclosed herein, any reference to direction or orientation is merely intended for convenience of description and is not intended in any way to limit the scope of the present disclosure. Relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. Terms such as "longitudinal" and "lateral" are to be interpreted relative to one another or relative to an axis of elongation, or an axis or center of rotation, as appropriate. These relative terms are for convenience of description only and do not require that the apparatus be constructed or operated in a particular orientation. Terms such as "attached," "affixed," "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship. The term "adjacent" as used herein to describe the relationship between structures/components includes both direct contact between the respective structures/components referenced and the presence of other intervening structures/components between respective structures/components. When only a single machine is illustrated, the term "machine" shall also be taken to include any collection of machines that individually or jointly execute a set (or multiple sets) of instructions to perform any one or more of the methodologies discussed herein. In the claims, means-plus-function clauses, if used, are intended to cover the structures described, suggested, or rendered obvious by the written description or drawings for performing the recited function, including not only structural equivalents but also equivalent structures. The terms "implant" and "device" are used interchangeably in this disclosure and such use should not limit the scope of the claims appended herewith.

As used herein, use of a singular article such as "a," "an" and "the" is not intended to exclude pluralities of the article's object unless the context clearly and unambiguously dictates otherwise.

Improved implants for hammer toe and/or claw toe correction are provided. Embodiments of the present subject matter provide a surgeon with a non-rigid construct and fusion of a joint after correction and a period of post-operative healing. Some embodiments can provide a rigid construct for initial post-operative wound healing and soft tissue release/relaxation while permitting predetermined motion back to the joint following a period of initial post-operative healing. Some embodiments can feature a proximal end of an implant including a ball portion and a distal end of the implant including a socket portion. A ball portion can include a portion of the implant having a surface of a suitable shape, including, but not limited to, a spherical, oval, cylindrical, or ellipsoidal shape, and permitting a predetermined movement of the ball portion when operatively connected to the socket portion. The inventors have observed that an implant having a ball portion and a socket portion can provide improved flexibility, stretching and movement at a respective joint post-insertion.

Figure 1B:
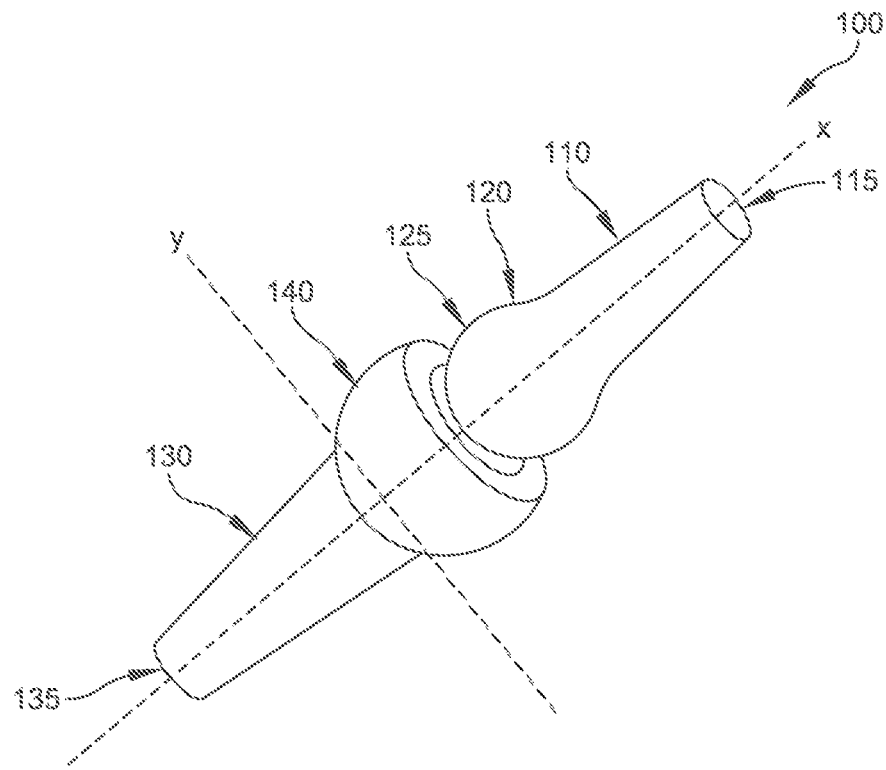
FIG. 1B is a perspective exploded view of the hammertoe implant shown in FIG. 1A.

FIG. 1A illustrates a front plan view of a toe bone implant according to some embodiments of the present disclosure. FIG. 1B illustrates a perspective view of a toe bone implant according to some embodiments of the present disclosure. With reference to FIGS. 1A and 1B, an implant 100 for correcting hammertoes can include a first portion 130 and a second portion 110. In the illustrated embodiment, the first portion 130 includes a socket portion 140 disposed at an edge of the first portion 130. The socket portion 140 can be formed of any suitable material. For example, the socket portion 140 can be formed of a polyethylene material. In some embodiments, a socket portion 140 material is selected to permit flexibility in the socket portion 140. In some embodiments, the socket portion 140 can be formed of a first material and the remainder of the first portion 130 can be formed of a second material. For example, the socket portion 140 can be formed of a polyethylene material and the remainder of the first portion 130 can be formed of a second material such as, for example, stainless steel, titanium, or other metals or rigid polymers.

As shown in FIGS. 1A and 1B, the second portion 110 can include a ball portion 120. Ball portion 120 can be formed of any suitable material. For example, ball portion 120 can be formed of a material such as stainless steel, titanium, or other metals or rigid polymers. In some embodiments, the second portion 110, including ball portion 120, can be formed of the same material. In other embodiments, the ball portion 120 can be formed of a first material and the remainder of the second portion 110 can be formed of a second material. In the illustrated embodiment, socket portion 140 can be configured to receive ball portion 120. In some embodiments, socket portion 140 and ball portion 120 include respective articulating surfaces 145, 125 such that ball portion 120 is configured to move a predetermined amount respective to the socket portion 140 when operatively connected to the socket portion 140. For example, socket portion 140 and ball portion 120 can include respective articulating surfaces 145, 125 such that ball portion 120 is configured to rotate a predetermined amount about an axis of rotation respective to the socket portion 140 when operatively connected to the socket portion 140. Ball portion 120 and socket portion 140 can be formed of any suitable shape. For example, a ball portion 120 can include an articulating surface 125 of a suitable shape, including, but not limited to, a spherical, oval, cylindrical, or ellipsoidal shape, and permitting a predetermined movement of the ball portion 120 when operatively connected to the socket portion 140. Socket portion 140 can include an articulating surface 145 of a suitable shape such as, for example, a spherical, oval, cylindrical, or ellipsoidal shape, such that ball portion 120 is configured to move a predetermined amount respective to the socket portion 140 when operatively connected to the socket portion 140.

FIGS. 1A and 1B illustrate a toe bone implant 100 prior to operatively connecting the ball portion 120 and the socket portion 140. In the illustrated embodiment, toe bone implant 100 is shown prior to insertion into a joint. Toe bone implant 100 can include an edge portion 135 of first portion 130 and an edge portion 115 of second portion 110. As shown, respective edge portions 135, 115 are on opposing edges of the socket portion 140 of first portion 130 and ball portion 120 of second portion 110. In some embodiments (not shown), implant 100 can include a resorbable portion operatively connected to the first 130 and second 110 portions and configured to limit the rotation of the ball portion 120 respective to the socket portion 140 for a predetermined period of time. Any suitable resorbable device can be used. For example, a resorbable pin, bridge, or lock out device can be used to limit the rotation of the ball portion 120 respective to the socket portion 140 for a predetermined period of time. Any suitable resorbable material can be used to form the resorbable portion. For example, a bioresorbable material including, but not limited to, polylactide (PLA), poly-L-lactide (PLLA), polyglycolide (PGA), co-polymers of PLA and PGA including PGLA, poly-DL-lactide (PDLLA), co-polymers thereof, or other suitable bioabsorble polymers, biopolymers or biodegradable polymers can be used to form the resorbable portion. In some embodiments, a resorbable snap on, lock out device can be used to hold the implant 100 in a predetermined initial position for a predetermined period of time. In some embodiments, a resorbable bridge that could cross a joint where the implant was inserted can be used to hold the implant 100 in a predetermined initial position for a predetermined period of time. In some embodiments, the predetermined period of time is an initial healing period. For example, an initial healing period could be approximately six weeks (e.g. 5-7 weeks). In some embodiments the predetermined period of time can be a period between approximately 8-12 weeks (e.g. 7-13 weeks). However, any suitable predetermined period of time can be used. The inventors have observed that an implant having rigid fixation for a predetermined period of time achieved through the use of a resorbable device, and after resorption, permitting a predetermined amount of rotation of a ball portion 120 of the implant 100 relative to the socket portion 140, can provide significant improvements to patients suffering from hammertoe or claw toe.

Figure 1C:
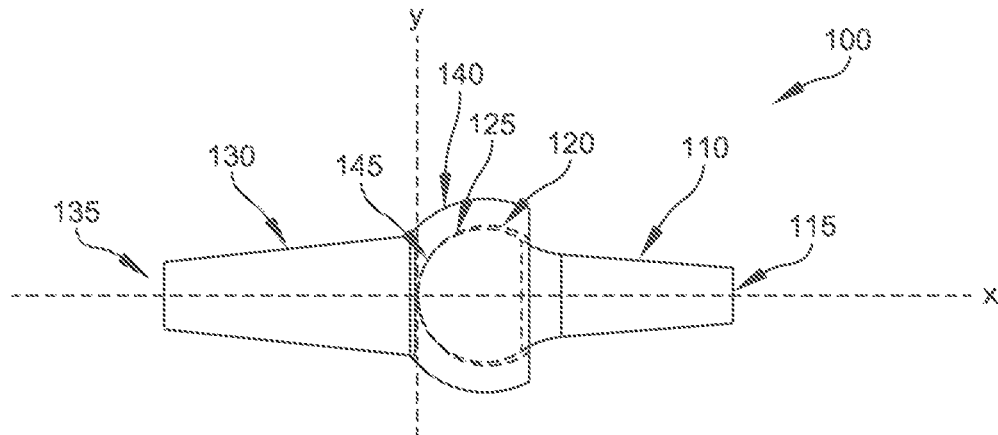
FIG. 1C is a side elevational view, partially in phantom, of the hammertoe implant shown in FIG. 1A.
Figure 1D:
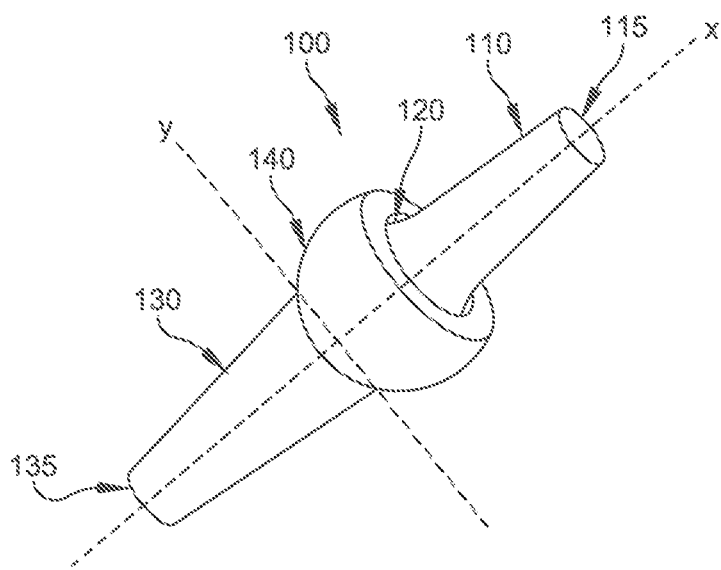
FIG. 1D is a perspective view of a hammertoe implant assembled in accordance with another embodiment of the invention.

Referring now to FIGS. 1C and 1D, a front plan view and a perspective view of a toe bone implant 100 are respectively provided after operatively connecting the ball portion 120 and the socket portion 140. In the illustrated embodiment, toe bone implant 100 is shown prior to insertion into a joint. In some embodiments, ball portion 120 can be configured to rotate a predetermined amount respective to socket portion 140 in a lateral direction (x). In some embodiments, ball portion 120 can be configured to rotate a predetermined amount respective to socket portion 140 about a lateral axis (x). In some embodiments, rotation in lateral direction (x) can be referred to as rotation in a plantar direction, e.g. toward the sole, i.e. at a substantially 90 degree angle between the front part of the foot and the shin In some embodiments, ball portion 120 can be configured to rotate a predetermined amount respective to socket portion 140 in a longitudinal direction (y). In some embodiments, ball portion 120 can be configured to rotate a predetermined amount respective to socket portion 140 about a longitudinal axis (y). In some embodiments, rotation in longitudinal direction (y) can be referred to as rotation in a dorsal direction, e.g. toward or away from a shin bone. In some embodiments, ball portion 120 can be configured to rotate a predetermined amount respective to socket portion 140 in a longitudinal direction (y) and a lateral direction (x). In some embodiments, ball portion 120 can be configured to rotate a predetermined amount respective to socket portion 140 about a longitudinal axis (y) and a lateral axis (x). In the illustrated embodiment, ball portion 120 is configured to freely rotate respective to socket portion 140.

Figure 1E:
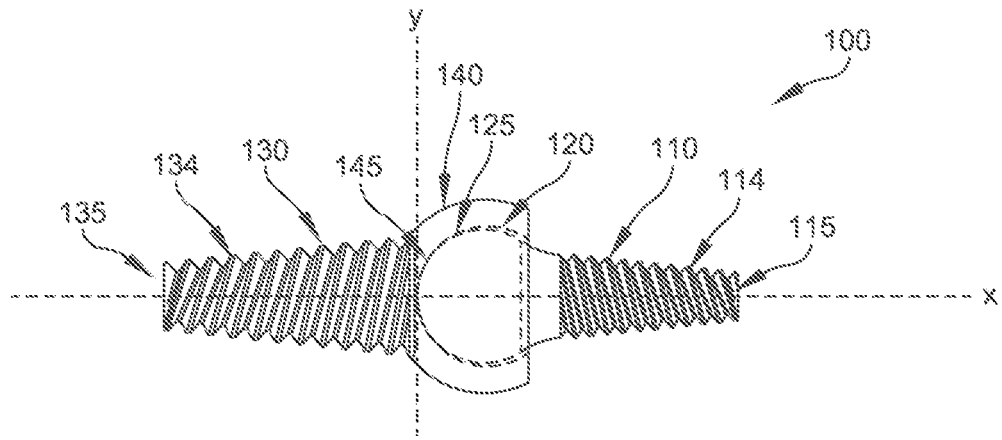
FIG. 1E is a side elevational view, partially in phantom, of a hammertoe implant including threaded portions.

With reference to FIG. 1E, a front plan view of a toe bone implant 100 according to some embodiments is provided. As shown in FIG. 1E, a portion of first portion 130 and a portion of second portion 110 can be threaded 134, 114. The threads 134, 114 may be threaded in substantially the same direction or in opposing directions. As ball portion 120 is configured to freely rotate respective to socket portion 140, both the respective first 130 and second 110 portions can be threaded into a respective bone canal. As shown, the threaded portion 134, 114 of first 130 and second 110 portions can include a plurality of threads disposed along its respective length. The tip (not shown) of respective threaded portions 134, 114 can be pointed to facilitate the advancement of threads 134, 114 into a respective bone. The respective edge portions 135, 115 can have any suitable type of interfacing mechanism to accept a suitable implant drivers such as a screw head or the like. In some embodiments, the respective edge portions 135, 115 can include a female depression (not shown) adaptable to mate with a driver (not shown) having a male extension. In some embodiments, for example, the respective edge portions 135, 115 1 can have a portion in the shape of a hex whereby a suitable driver has a corresponding hex adapter appropriate to drive the implant 100 into a respective bone.

Figure 1F:
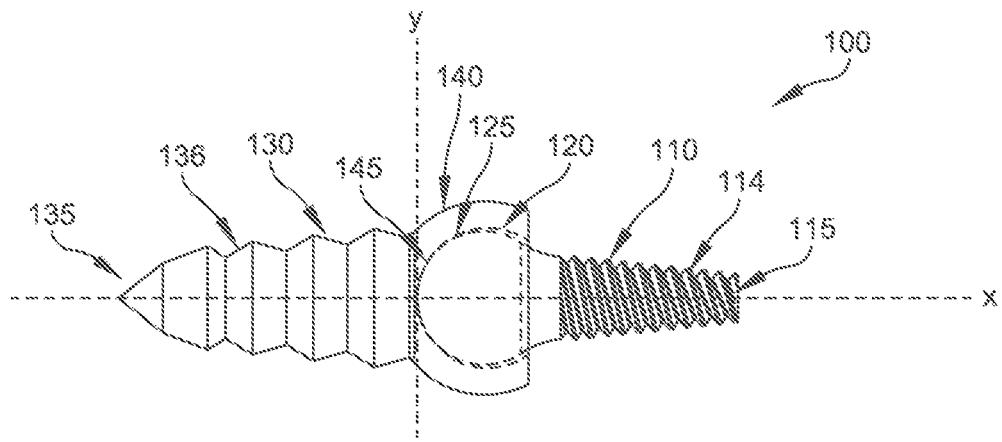
FIG. 1F is a side elevational view of a further embodiment of hammertoe implant formed in accordance with the another embodiment of the invention including a blade portion and a threaded portion.

Referring now to FIG. 1F, a front plan view of an implant 100 is shown according to some embodiments of the present disclosure. In the illustrated embodiment, a portion of first portion 130 includes blades 136 to improve alignment or implantation while inserting the first portion 130 into a bone canal. As shown, blade portion 136 includes a plurality of serrated edges on its top and bottom sides. In some embodiments, blade portion 136 can have a width that is greater than its thickness and can taper to a point. In some embodiments such as embodiments using a resorbable pin, a portion of first portion 130 can include blades 136 to improve alignment or implantation while inserting the first portion 130 into a bone canal. In some embodiments (not shown), a portion of first portion 130 can include barbs 136 to improve alignment or implantation while inserting the first portion 130 into a bone canal.

In various embodiments, an implant 100 can be implanted into targeted bones by any suitable method. For example, an implant 100 can be implanted or installed via a retrograde approach between, for example, proximate and middle phalanxes in a foot. One skilled in the art will understand that the method described herein may be applied to the middle and distal phalanxes, respective metatarsals, as well or other adjacent bones. In some embodiments, an implant 100 can be implanted via a retrograde approach between, for example, a phalanx and a metatarsal in a foot. In some embodiments, a driver can be used to implant an implant 100 into a joint. For example, a driver can be an elongated instrument and include one end having an adaptable portion suitable for mating with an implant 100 described above. In some embodiments, the adaptable portion can include a male hexagonal head adaptable to mate to a corresponding female depression in an edge portion 135, 115 of an implant 100. In some embodiments, an opposing end of the driver can include a driving pin or trocar and can include a flat modular section configured to accept a handle or other suitable mechanism to assist a surgeon during installation of an implant 100.

Figure 7:
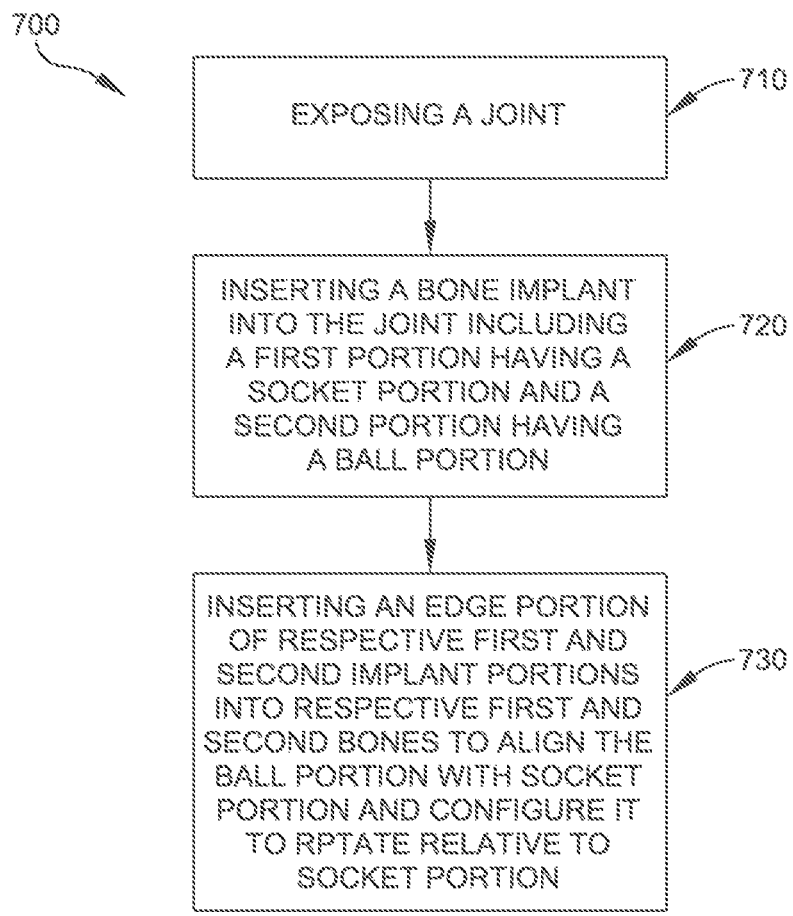
FIG. 7 is a flow chart illustrating a method of correcting a toe bone deformity according to embodiments of the present disclosure.

Referring now to FIG. 7, a flow chart showing a method of correcting a toe bone deformity is provided. At block 710, a joint is exposed between first and second bones. In some embodiments, the joint is a proximal interphalangeal (PIP) joint. In some embodiments, the joint is a distal interphalangeal (DIP) joint. In some embodiments, the joint is a metatarsal phalangeal joint. In some embodiments, a toe can be opened to provide access to a joint between a first bone and a second bone. For example, a toe can be opened to provide access to a joint between a middle phalanx and a proximal phalanx, or, for example, between a distal phalanx and a proximal metatarsal. In some embodiments, an incision is made to open the joint. In some embodiments, the first and/or second bones, respectively, may be resected using a bone saw or other tool, if necessary. The resected surfaces of the first and/or second bones can be debrided if necessary. At block 720, bone implant 100 can be inserted into the joint. Any suitable insertion method can be used. At block 730, an edge portion 135, 115 of respective first 130 and second 110 implant portions is inserted into respective first and second bones. Any suitable method to insert the respective edge portions 115, 135 into first and second bones. For example, an intermedullary canal can be drilled into one or both of the first and second bones using a drill or other mechanism to an appropriate depth. In some embodiments, a reamer can be used for precise and accurate canal drilling. In some embodiments, a driver can be engaged with an edge portion 135 of the first portion 130 of an implant 100 as described above, and an edge portion 115 of the second portion 110 of the implant 100 can be threaded into the first bone. In some embodiments, bladed portion 136 of first portion 130 can be disposed within a slot of a driving adapter and the body of the driving adapter can be secured in a chuck of a drill or other driving instrument. A drill or other driving instrument can be used to drive threaded portion 114 of second portion 110 into a surface of a second bone, for example, a proximal metatarsal. With the threaded portion 114 of second portion 110 of implant 100 disposed within second bone, a driving adapter can be disengaged from blade portion 136 of first portion 130 of implant 100.

The first bone, for example a distal phalanx, can be predrilled or broached using a drill, or other suitable device, to create a hole. In some embodiments, a reamer can be used for precise drilling or broaching The predrilled or broached first bone is then repositioned such that the predrilled hole or broach aligns with the blade portion 136 of first portion 130 of implant 100. The first bone is then pressed into engagement with the blade portion 136 of first portion 130. The serrated edges of blade portion 136 of first portion 130 help to maintain engagement between first bone and blade portion 136 of first portion 130 of implant 100. In some embodiments, a ball portion 120 of second portion 110 can be operatively connected to a socket portion 140 of first portion 130 in situ. In some embodiments, a ball portion 120 of second portion 110 can be operatively connected to a socket portion 140 of first portion 130 prior to insertion of toe implant 100 into the joint. At block 740, the ball portion 120 is aligned with socket portion 140 such that ball portion 120 is configured to rotate a predetermined amount relative to socket portion 140. In some embodiments (e.g. FIGS. 2, 3, 4, 6), a ball portion of a second portion can be operatively connected to a socket portion of a first portion in situ. In some embodiments, the respective edge portions of ball portion 120 of second portion 110 and socket portion 140 of first portion 130 are inserted into respective first and second bones such that the ball portion 120 is aligned with socket portion 140 and is configured to rotate a predetermined amount relative to the socket portion 140.

Figure 2A:
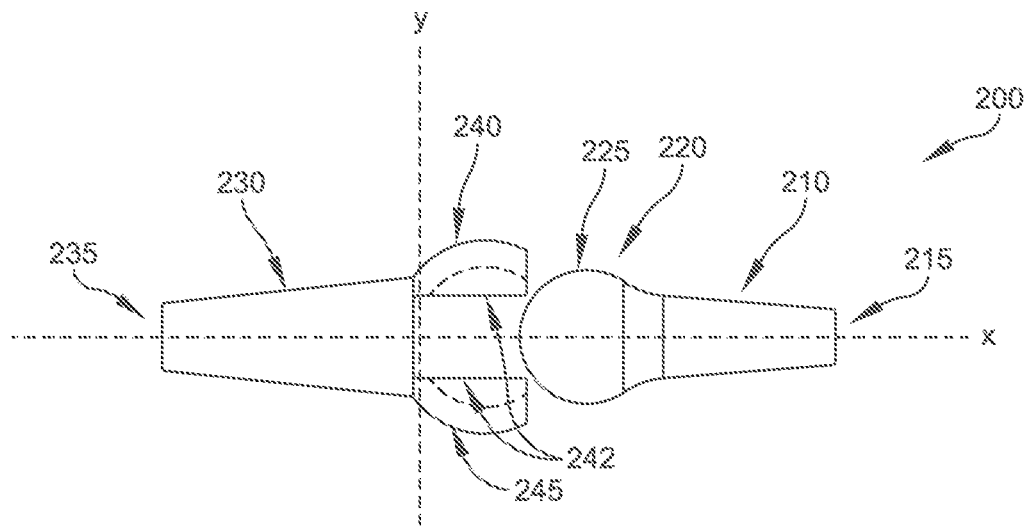
FIG. 2A is a side elevational view of an alternative embodiment of hammertoe implant including a socket portion, having both spherical and cylindrical articulating surfaces.
Figure 2B:
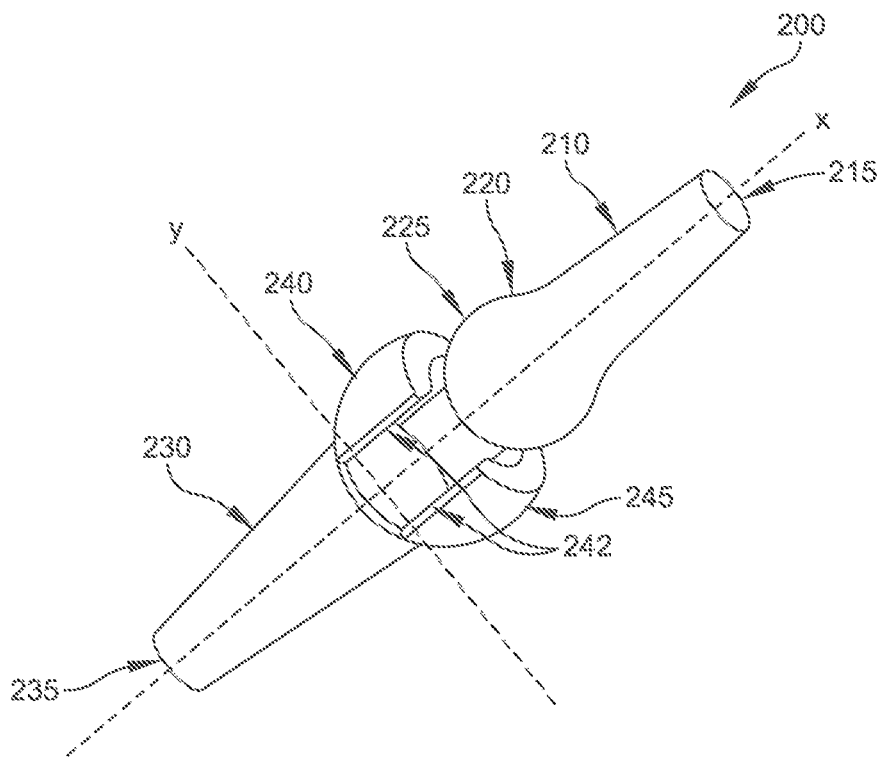
FIG. 2B is a perspective view of the hammertoe implant shown in FIG. 2A.
Figure 2C:
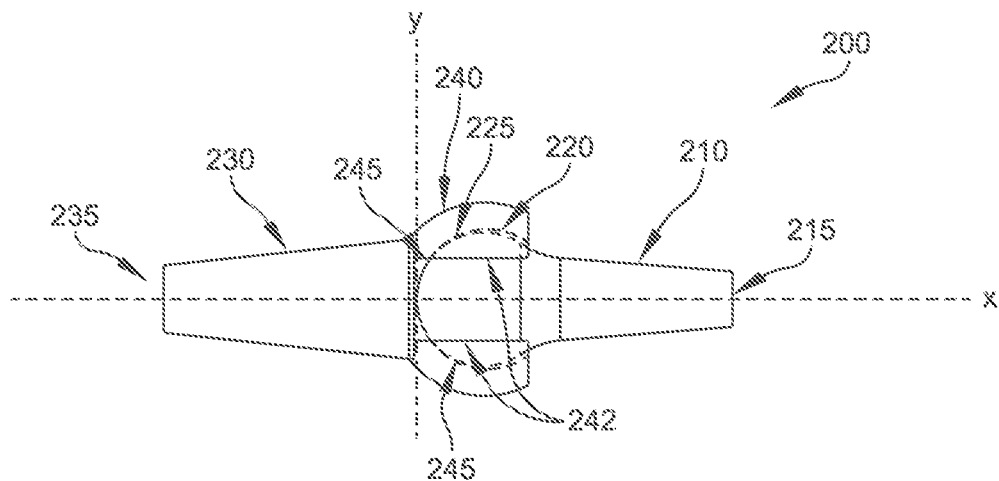
FIG. 2C is a side elevational view, partially in phantom, of an assembled hammertoe implant in accordance with FIGS. 2A and 2B.
Figure 2D:
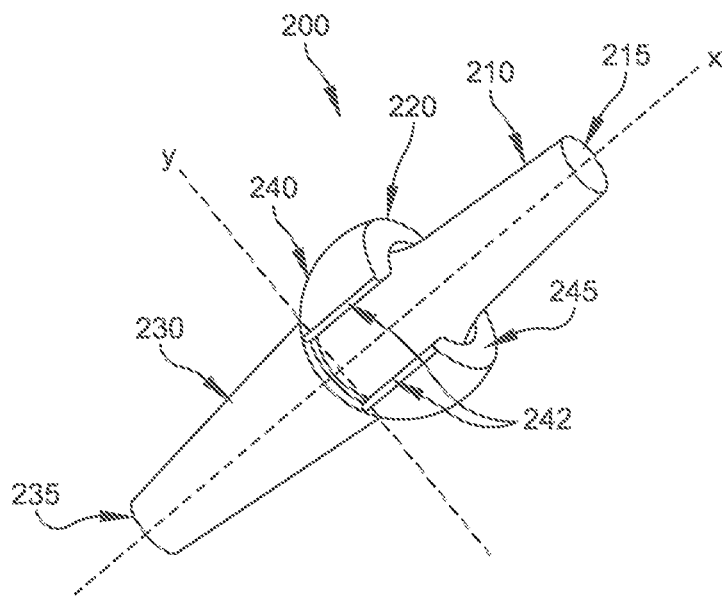
FIG. 2D is a perspective view of the hammertoe implant shown in FIG. 2C.

With reference now to FIGS. 2A-2F, various plan and perspective views of an implant 200 according to some embodiments of the present disclosures are provided. In the illustrated embodiment, the first portion 230 and second portion 210 can be inserted (720) into a joint independent of each other. The ball portion 220 can be operatively connected to the socket portion 240 in situ. As shown and described above, socket portion 240 is formed of a material flexible enough to allow insertion and operative connection of the ball portion 220 of second portion 210. In some embodiments, the force required to insert ball portion 220 into socket portion 240 is less than the force required to remove ball portion 220 from socket portion 240. As shown in FIGS. 2B -2F, ball portion 220 will not detach from socket portion 240. With reference now to FIGS. 2B and 2D, both spherical 225, 245 and cylindrical 242 articulating surfaces can be provided on the ball portion 220 and socket portion 240 to limit the rotation of the ball portion 220 relative to the socket portion 240 to dorsi/plantar flexion. In some embodiments, where the predetermined amount of rotation of the ball portion 220 relative to socket portion 240 is limited to dorsiflexion, a greater amount of material can be added to the plantar portion of socket portion 240 of the first portion 230 of implant 200.

Figure 2E:
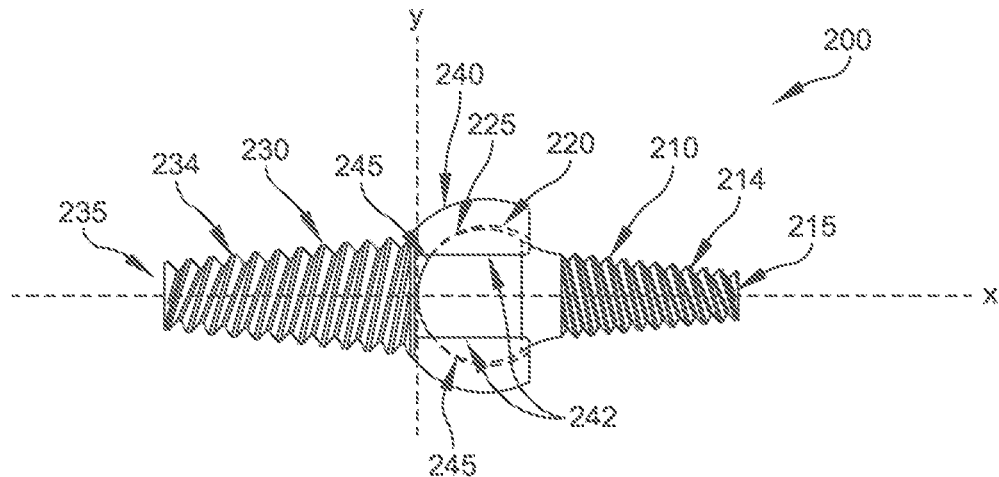
FIG. 2E is a side elevational view, partially in phantom, of a hammertoe implant in accordance with FIG. 2A, including with threaded portions.
Figure 2F:
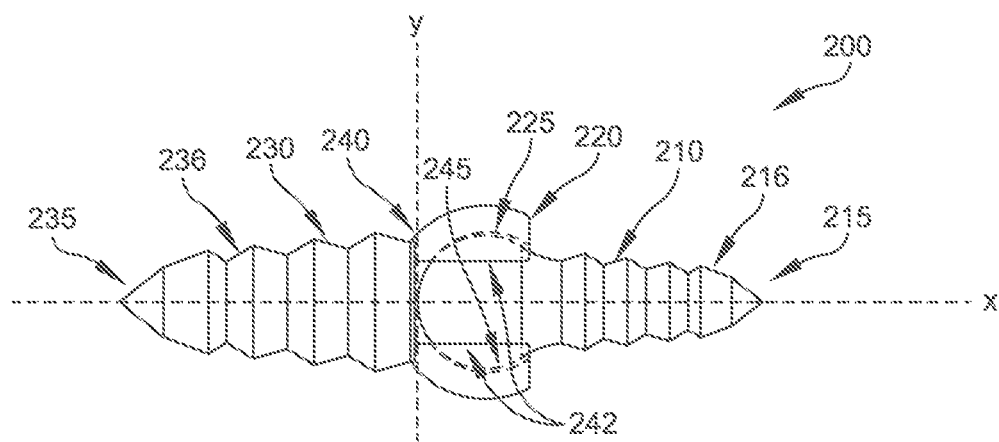
FIG. 2F is a side elevational view, partially in phantom, of a hammertoe implant in accordance with the embodiment of FIG. 2A, having blade portions.

In some embodiments, an open procedure can be used to expose a joint (710), for inserting the implant 200 into the joint, and for soft tissue release. As discussed above, first and second bones can be resected in some embodiments. In some embodiments, a reamer can be used to for accurate and precise drilling of a canal into respective first and second bones. As shown in FIG. 2E, first 230 and second 210 portions can include respective threaded portions 234, 214. In some embodiments, respective edge portions 235, 215 can be threaded into canals as described above (715) as the first 230 and second 210 portions are implanted independently and operatively connected in situ. As shown in FIG. 2F, first 230 and second 210 portions can include respective bladed portion 236, 216. In some embodiments, respective edge portions 235, 215 can be inserted into respective first and second bones independently and ball portion 220 inserted into and operatively connected to socket portion 240 in situ to align ball portion 220 with socket portion 240 and configure it to rotate a predetermined amount relative to socket portion 240. In some embodiments (not shown), implant 200 can include a resorbable portion operatively connected to the first 230 and second 210 portions and configured to limit the rotation of the ball portion 220 respective to the socket portion 240 for a predetermined period of time as described above.

Figure 3A:
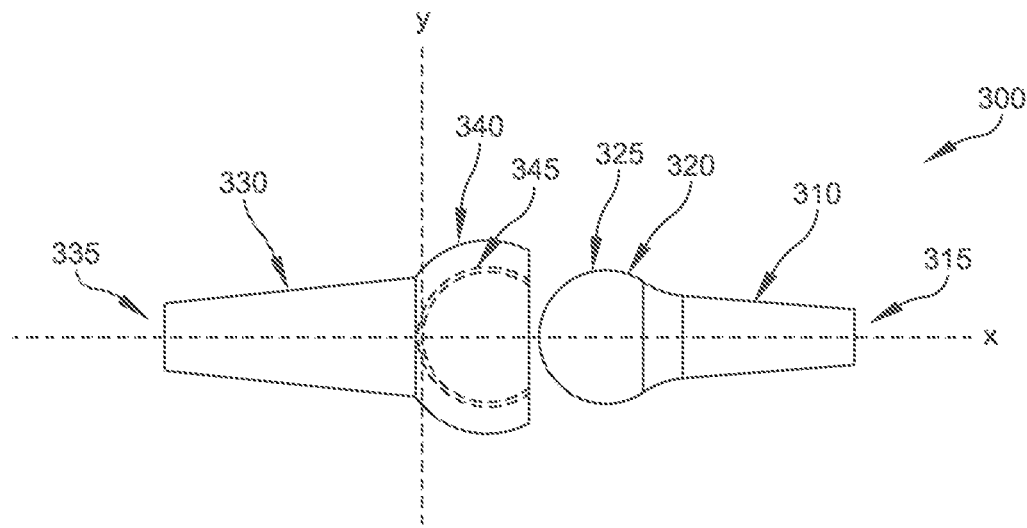
FIG. 3A is a side elevational, partially exploded, and partially in phantom further embodiment of a hammertoe implant formed in accordance with the invention having spherical and cylindrical articulating surfaces.
Figure 3B:
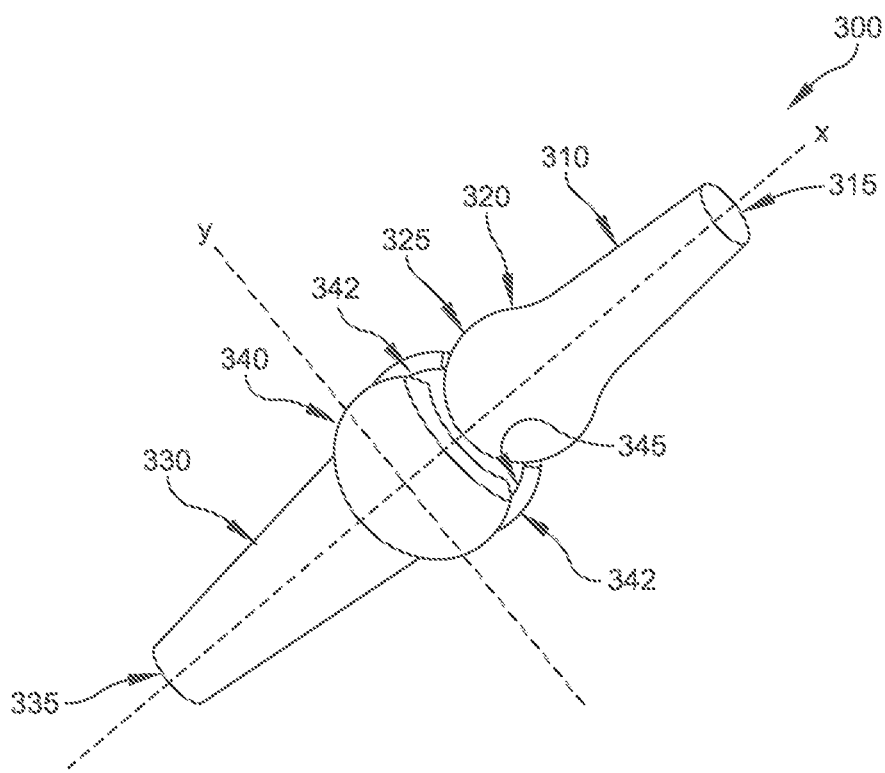
FIG. 3B is a perspective view, partially exploded, of the hammertoe implant shown in FIG. 3A.
Figure 3C:
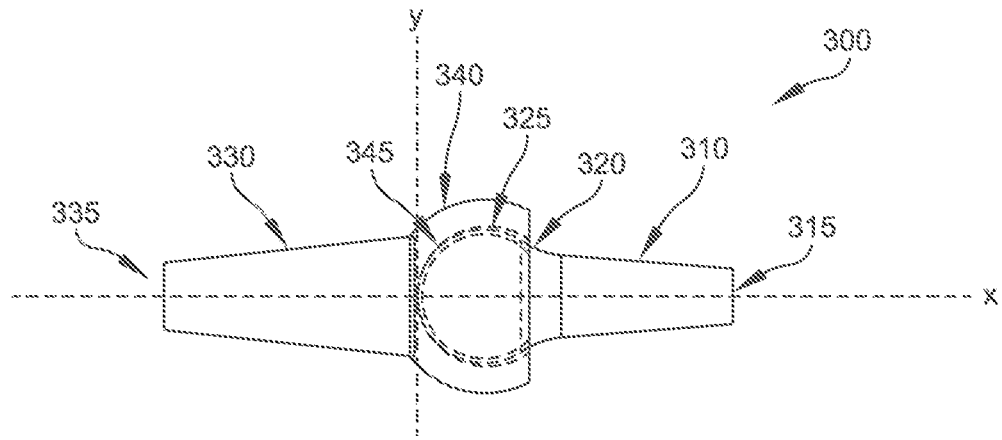
FIG. 3C is a side elevational view, partially in phantom, of an assembled hammertoe implant in accordance with FIGS. 3A and 3B.
Figure 3D:
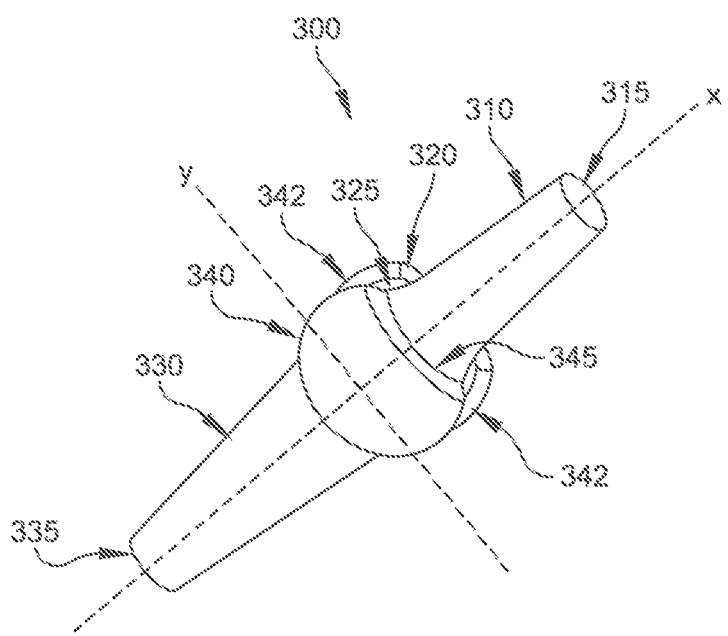
FIG. 3D is a perspective view of the hammertoe implant shown in FIG. 3C.

Referring now to FIGS. 3A-3F, various plan and perspective views of implant 300 are provided according to some embodiments of the present disclosure. As shown in FIGS. 3B and 3D, both spherical 325, 345 and cylindrical 342 articulating surfaces can be provided on the ball portion 320 and socket portion 340 to limit the rotation of the ball portion 320 relative to the socket portion 340 to dorsi/plantar flexion. In some embodiments, where the predetermined amount of rotation of the ball portion 320 relative to socket portion 340 is limited to dorsiflexion, a greater amount of material can be added to the plantar portion of socket portion 340 of the first portion 330 of implant 300. As shown in the illustrated embodiments of 2B, 2D, 3B and 3D, there is less dorsal/plantar constraint in the embodiments illustrated in FIGS. 3B and 3D and more dorsal/plantar constraint in the embodiments shown in FIGS. 2B and 2D.

Figure 3E:
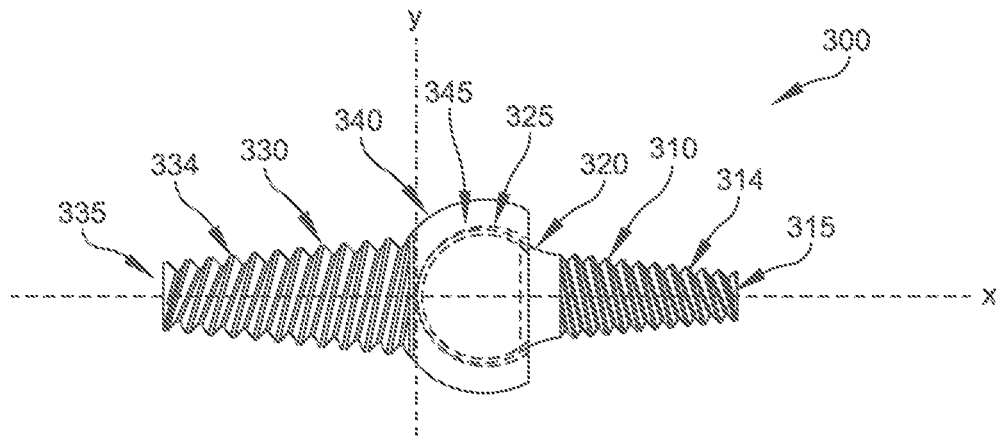
FIG. 3E is a side elevational view, partially in phantom, of the hammertoe implant shown in FIGS. 3A-3D including threaded portions.
Figure 3F:
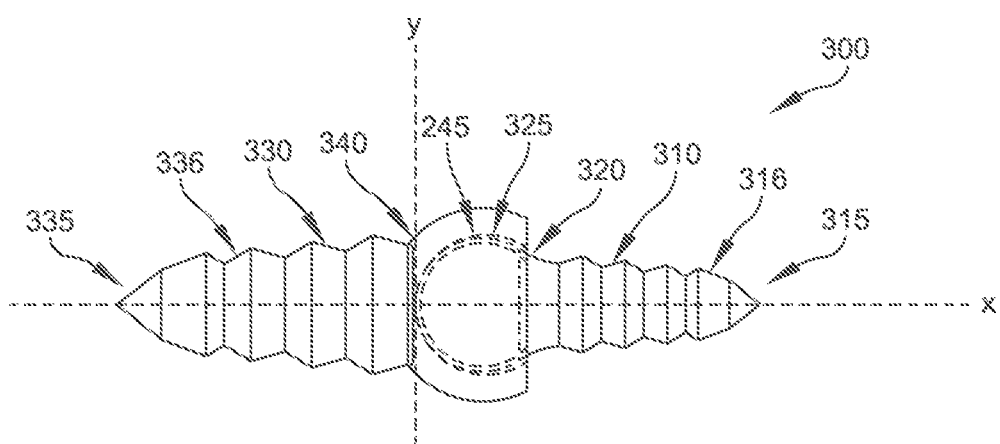
FIG. 3F is a side elevational view, partially in phantom, of the hammertoe implant shown in FIGS. 3A-3D, and including blade portions.

In some embodiments, an open procedure can be used to expose a joint (710), for inserting the implant 300 into the joint, and for soft tissue release. As discussed above, first and second bones can be resected in some embodiments. In some embodiments, a reamer can be used to for accurate and precise drilling of a canal into respective first and second bones. As shown in FIG. 3E, first 330 and second 310 portions can include respective threaded portions 334, 314. In some embodiments, respective edge portions 335, 315 can be threaded into canals as described above (715) as the first 330 and second 310 portions are implanted independently and operatively connected in situ. As shown in FIG. 2F, first 330 and second 310 portions can include respective bladed portion 336, 316. In some embodiments, respective edge portions 335, 315 can be inserted into respective first and second bones independently and ball portion 320 inserted into and operatively connected to socket portion 340 in situ to align ball portion 320 with socket portion 340 and configure it to rotate a predetermined amount relative to socket portion 340. In some embodiments (not shown), implant 300 can include a resorbable portion operatively connected to the first 330 and second 310 portions and configured to limit the rotation of the ball portion 320 respective to the socket portion 340 for a predetermined period of time as described above.

Figure 4A:
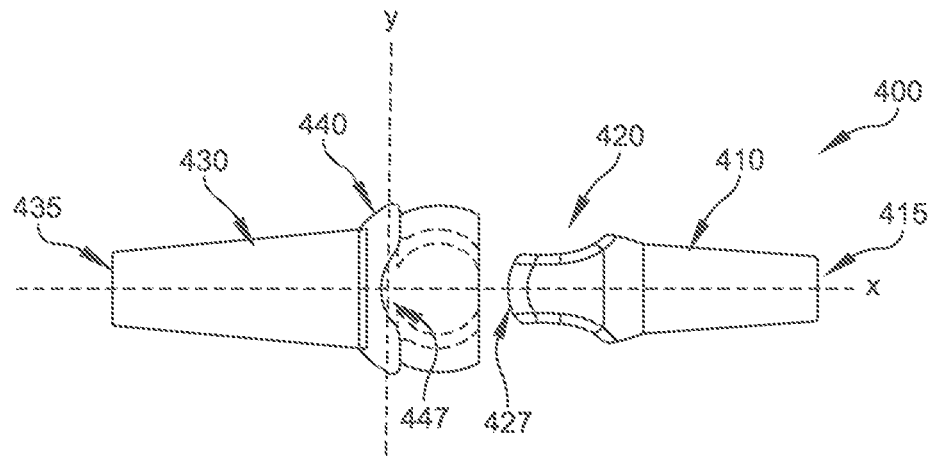
FIG. 4A is an exploded side elevational view, partially in phantom, of a further alternative embodiment of hammertoe implant including a cylindrical articulating surface and corresponding ball portion.
Figure 4B:
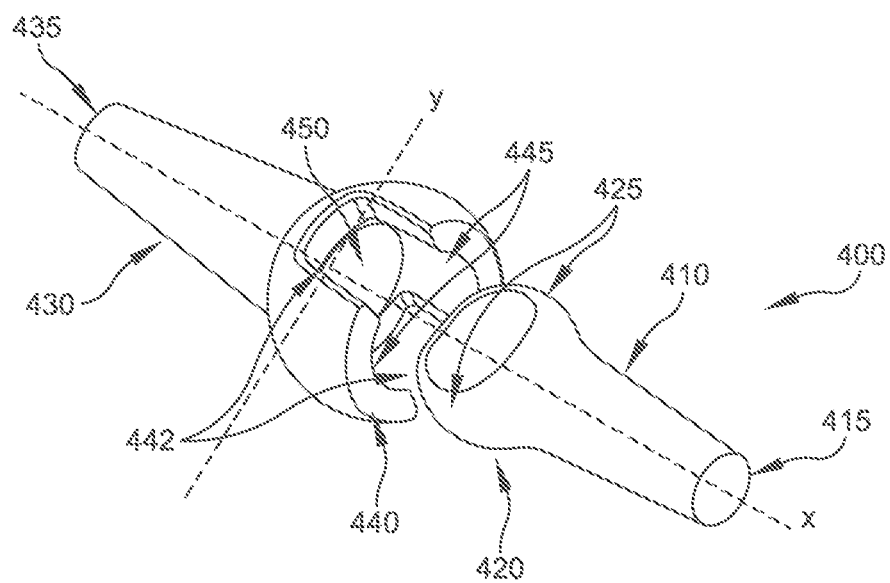
FIG. 4B is a perspective view of the hammertoe implant shown in FIG. 4A.
Figure 4C:
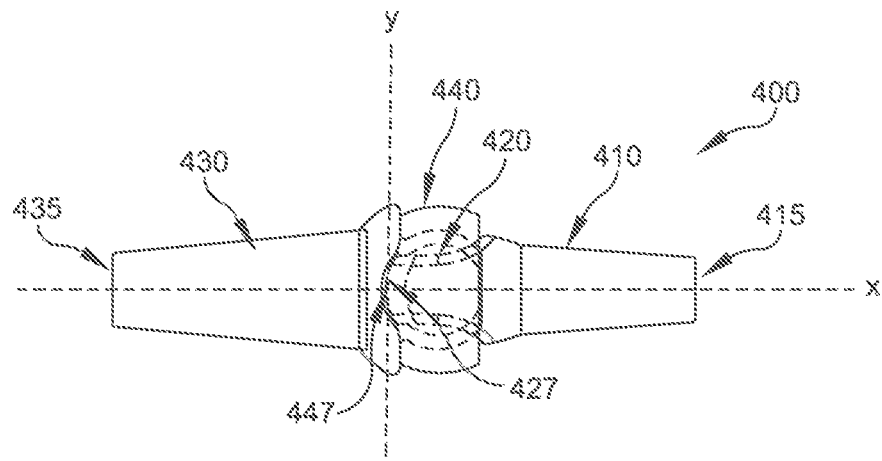
FIG. 4C is a side elevational view, partially in phantom, of the hammertoe implant shown in FIGS. 4A and 4B.
Figure 4D:
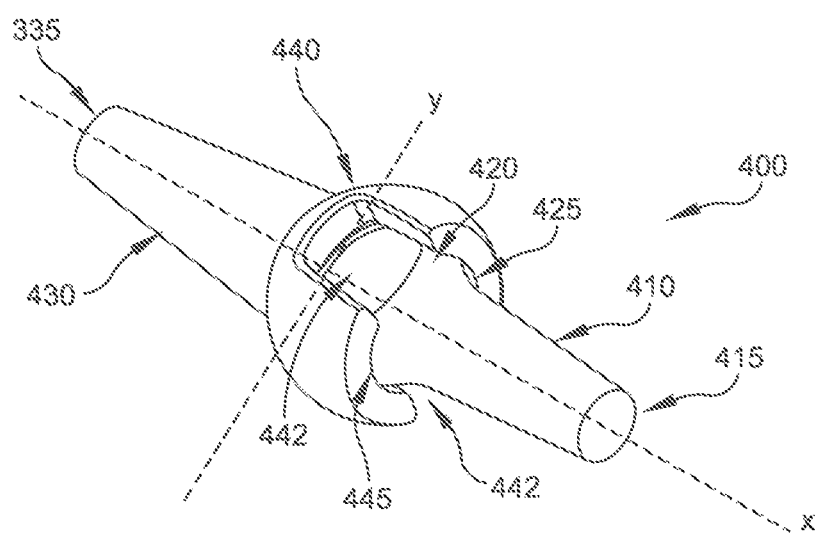
FIG. 4D is a perspective view of the hammertoe implant shown in FIG. 4C.

Referring now to FIGS. 4A-4E, various plan and perspective views of an implant 400 are provided according to some embodiments of the present disclosure. As illustrated in FIGS. 4A and 4C, ball portion 420 and socket portion 440 can include respective cylindrical articulating surfaces 427, 447 and respective spherical articulating surfaces 445, 425 to limit the rotation of the ball portion 420 relative to the socket portion 440 to a predetermined amount. In the illustrated embodiment, interior portion 450 formed in socket portion 440 along with respective cylindrical articulating surfaces 427, 447 and respective spherical articulating surfaces 445, 425 creates a hinge type of implant 400 and limits rotation of the ball portion 420 relative to socket portion 440 to dorsal/plantar flexion. In some embodiments, where the predetermined amount of rotation of the ball portion 420 relative to socket portion 440 is limited to dorsiflexion, a greater amount of material can be added to the plantar portion of socket portion 440 of the first portion 430 of implant 400.

Figure 4E:
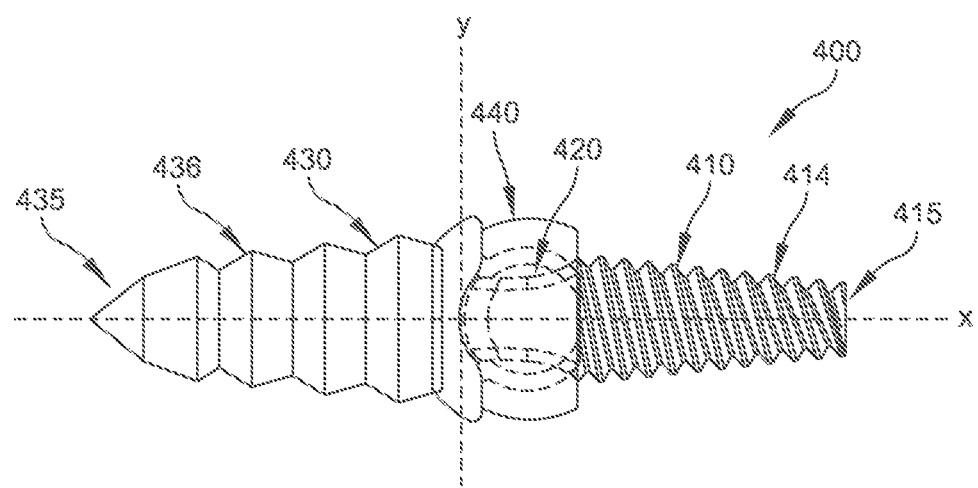
FIG. 4E is a side elevational view, partially in phantom, of a hammertoe implant in accordance with FIG. 4A showing a threaded portion and a blade portion.

In some embodiments, an open procedure can be used to expose a joint (710), for inserting the implant 400 into the joint, and for soft tissue release. As discussed above, first and second bones can be resected in some embodiments. In some embodiments, a reamer can be used to for accurate and precise drilling of a canal into respective first and second bones. In some embodiments (not shown), first 430 and second 410 portions can include respective threaded portions (not shown). In some embodiments (not shown), respective edge portions 435, 415 can be threaded into canals as described above (715) as the first 430 and second 410 portions are implanted independently and operatively connected in situ. As shown in FIG. 4E, in some embodiments, first portion 430 can include a bladed portion 436 and second portion 410 can include a threaded portion 414 and respective edge portions 435, 415 can be threaded into canals as described above (715) as the first 430 and second 410 portions are implanted independently and operatively connected in situ. In some embodiments (not shown), first 430 and second 310 portions can include respective bladed portions. In some embodiments (not shown), first 430 and second 310 portions can include respective barbed portions. In some embodiments, respective edge portions 435, 415 can be inserted into respective first and second bones independently and ball portion 420 inserted into and operatively connected to socket portion 440 in situ to align ball portion 420 with socket portion 440 and configure it to rotate a predetermined amount relative to socket portion 440. In some embodiments (not shown), implant 400 can include a resorbable portion operatively connected to the first 430 and second 410 portions and configured to limit the rotation of the ball portion 420 respective to the socket portion 440 for a predetermined period of time as described above.

Figure 5A:
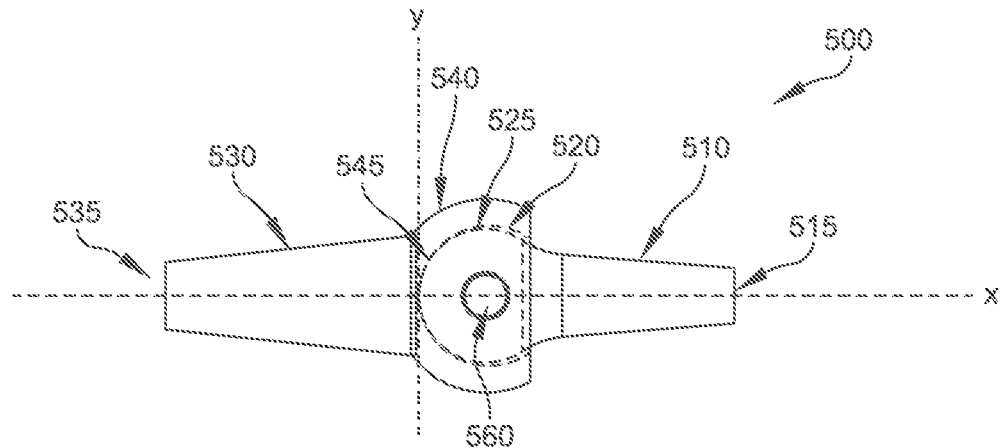
FIG. 5A is a side elevational view, partially in phantom, of a further alternative embodiment of hammertoe implant including a ball portion and a socket portion that together accommodate a cross pin.
Figure 5B:
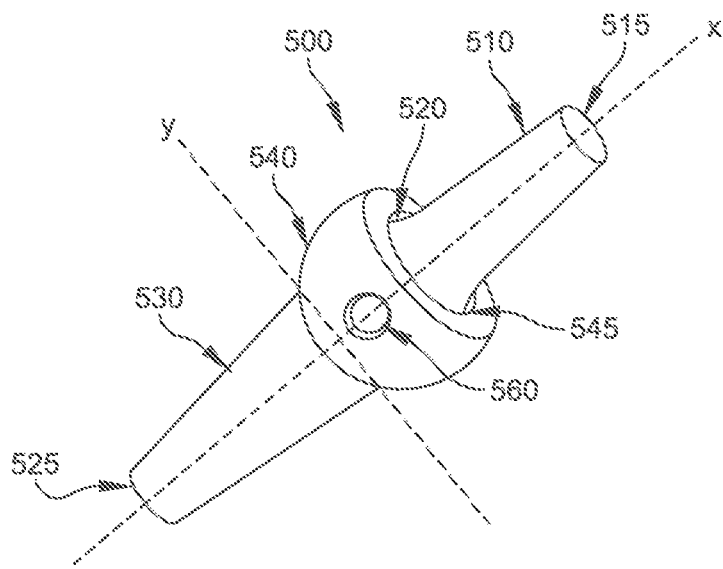
FIG. 5B is a perspective view of the hammertoe implant shown in FIG. 5A.
Figure 5C:
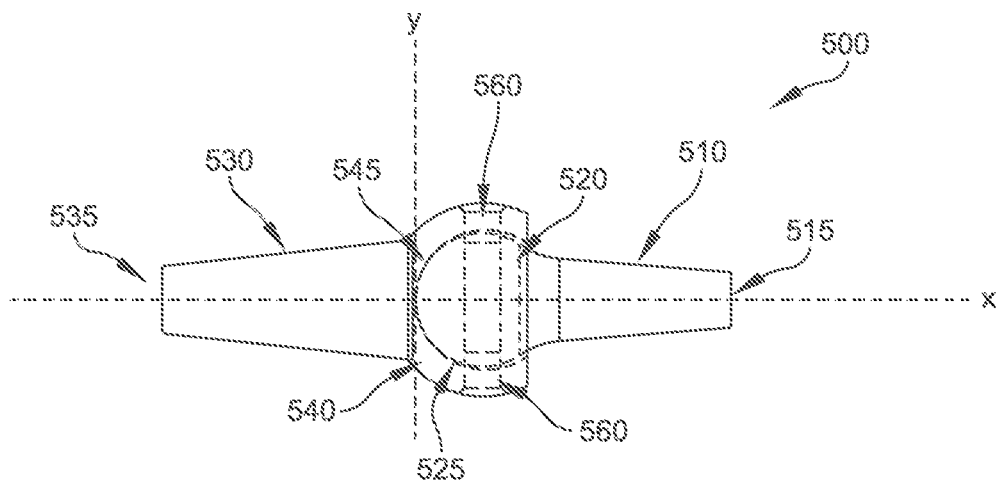
FIG. 5C is a side elevational view, partially in phantom, of the hammertoe implant of FIGS. 5A and 5B including a cross pin shown in phantom.
Figure 5D:
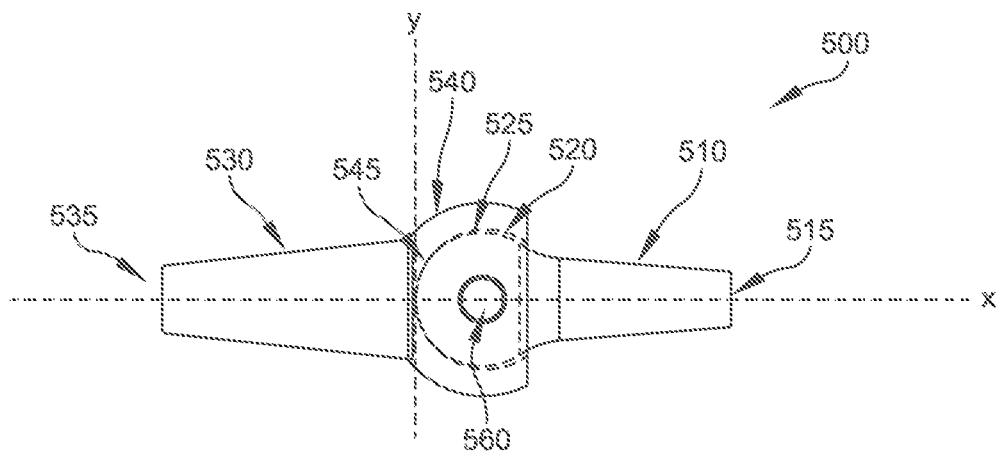
FIG. 5D is a side elevational view, partially in phantom, of the hammertoe implant shown in FIG. 5C but rotated 90° about axis X.

Referring now to FIGS. 5A-5D, various plan and perspective views of a hinge type bone implant 500 according to some embodiments of the present disclosure are provided. In the illustrated embodiments, the ball portion 520 is inserted into the socket portion 540 prior to inserting the bone implant 500 into a joint (720). As shown in the illustrated embodiment, a cross pin 560 can be inserted between the ball portion 520 and the socket portion 540 to limit rotation of the ball portion 520 relative to the socket portion 540 to dorsi/plantar flexion. In some embodiments, the ball portion 520 can be disposed asymmetrically relative to the socket portion 540 to further limit rotation to a predetermined amount. In some embodiments, and as shown in FIG. 5C, resorbable cross-pin ends 565 can be included to restrict rotation of the ball portion 520 relative to the socket portion 520 for a predetermined period of time as described above. In some embodiments, where the predetermined amount of rotation of the ball portion 520 relative to socket portion 540 is limited to dorsiflexion, a greater amount of material can be added to the plantar portion of socket portion 540 of the first portion 530 of implant 500.

In some embodiments, an open procedure can be used to expose a joint (710), for inserting the implant 500 into the joint, and for soft tissue release. As discussed above, first and second bones can be resected in some embodiments. In some embodiments, a reamer can be used to for accurate and precise drilling of a canal into respective first and second bones. In some embodiments (not shown), one of the first 530 or second 510 portions can include a respective threaded portions (not shown) as the implant 500 is assembled prior to insertion into a joint. In some embodiments (not shown), the respective edge portion 435 (or 415) of the respective portion including a threaded portion can be threaded into a respective canal as described above (715). In some embodiments, the other one of the first 530 or second 510 portions of the implant 500 can include a bladed portion. In some embodiments, the other one of the first 530 or second 510 portions of the implant 500 can include a barbed portion.

Figure 6A:
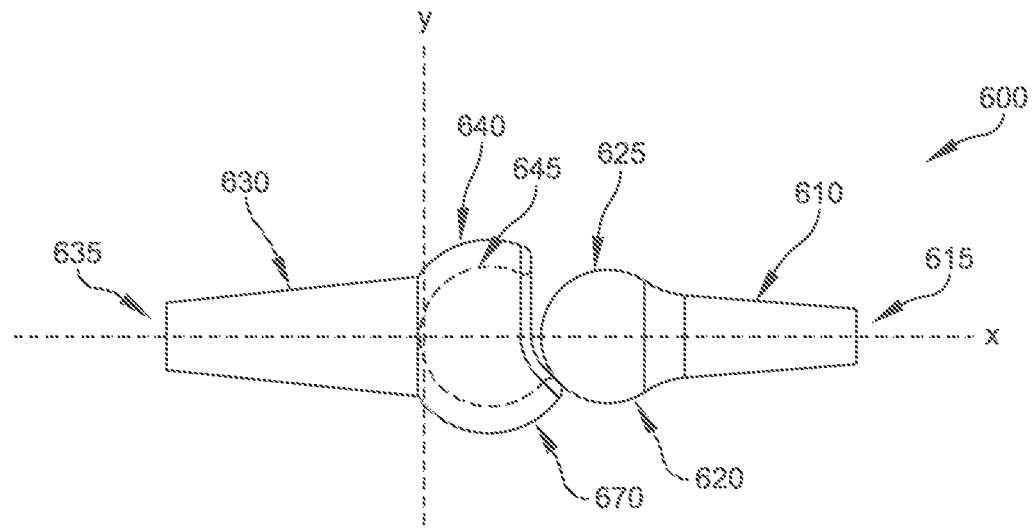
FIG. 6A is a side elevational view, partially in phantom, of yet a further alternative embodiment of hammertoe implant formed in accordance with the invention showing a flange portion included in a socket portion to limit rotation of a ball portion.
Figure 6B:
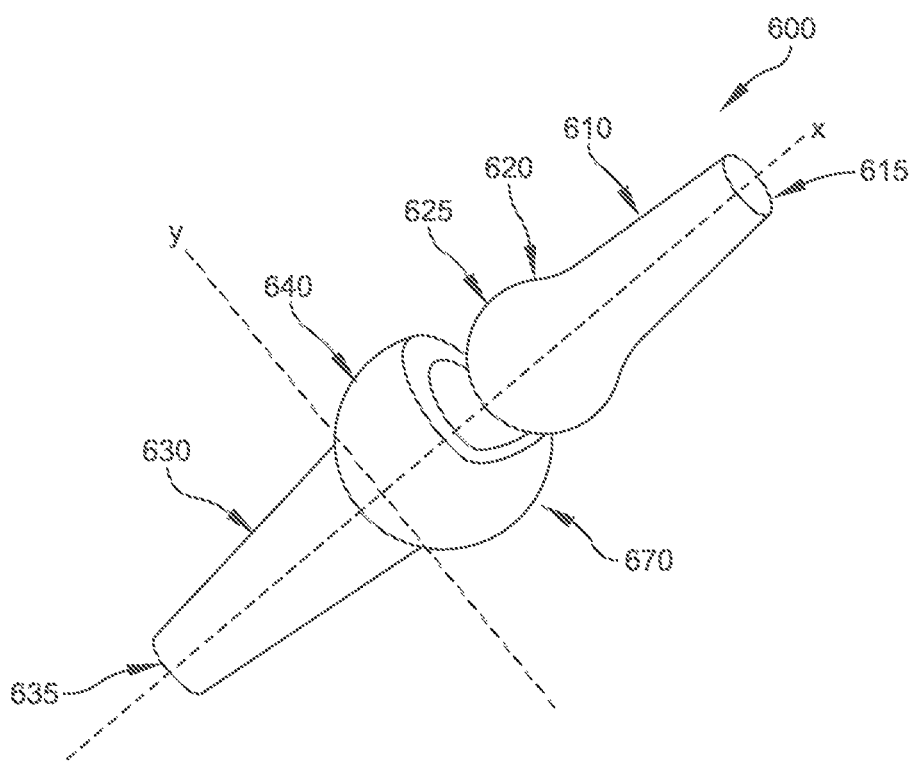
FIG. 6B is a perspective view of a hammertoe implant shown in FIG. 6A.
Figure 6C:
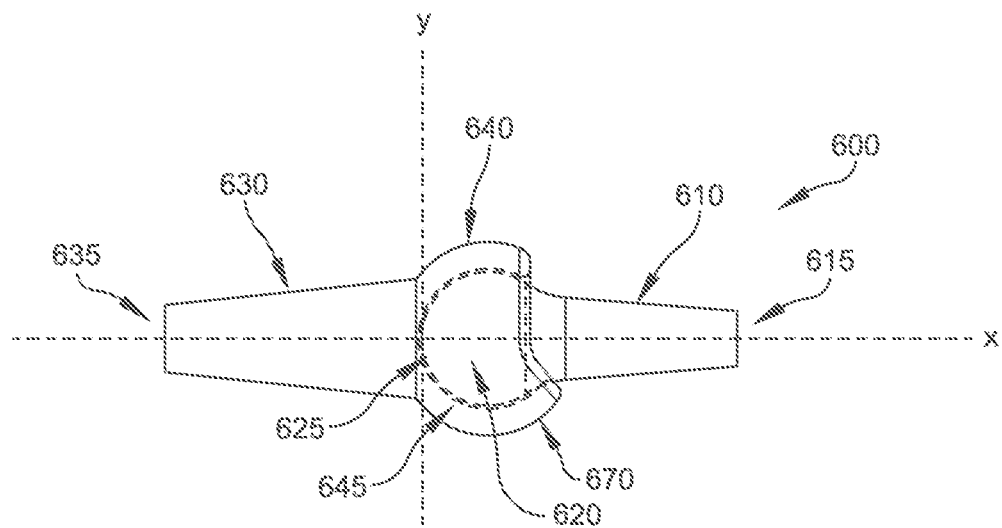
FIG. 6C is a side elevational view, partially in phantom, of an assembled hammertoe implant in accordance with FIGS. 6A and 6B.
Figure 6D:
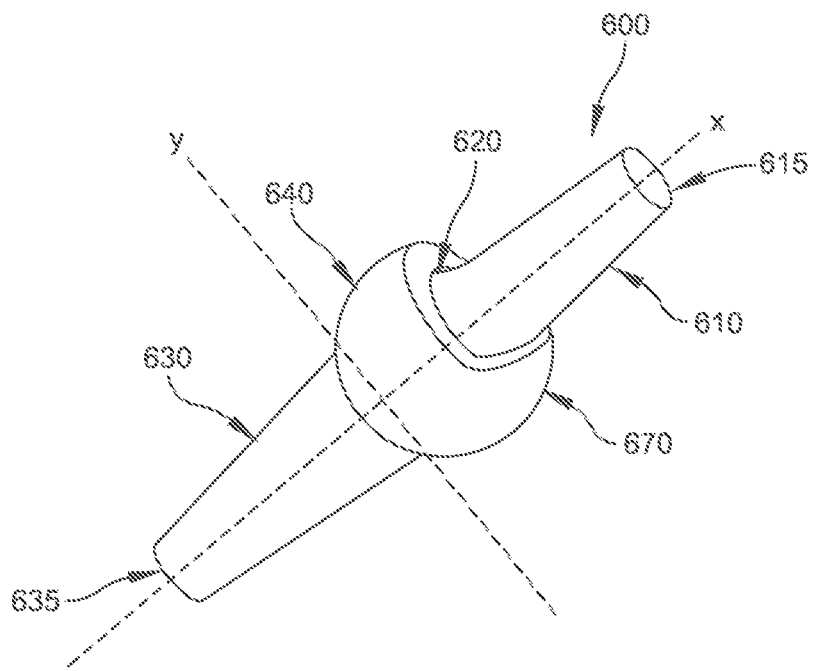
FIG. 6D is a perspective view of the hammertoe implant shown in FIG. 6C.
Figure 6E:
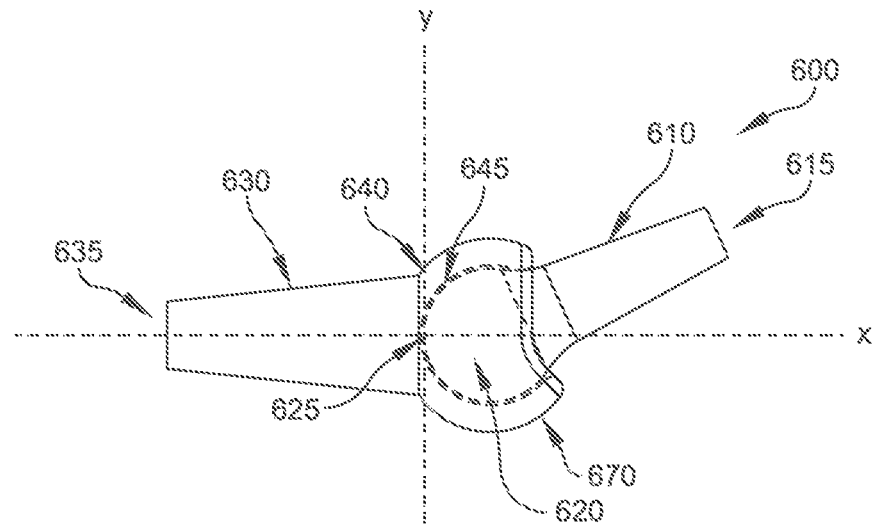
FIG. 6E is a side elevational view, partially in phantom, of the hammertoe implant shown in FIGS. 6A-6D with the ball portion rotated within the socket portion at an angle relative to axes X and Y.
Figure 6F:
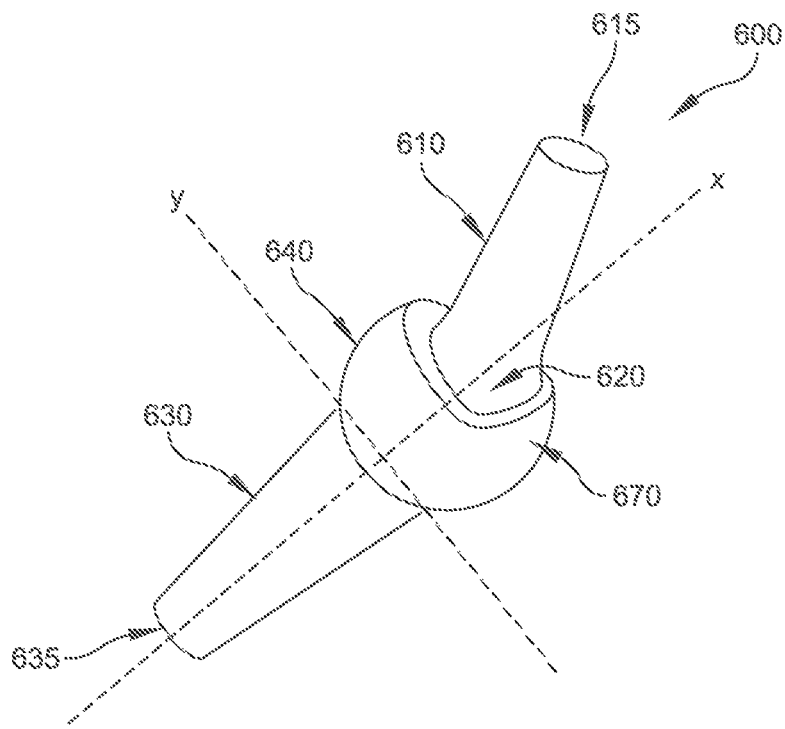
FIG. 6F is a perspective view of the hammertoe implant shown in FIG. 6E.

With reference now to FIGS. 6A-6H, various plan and perspective views of an implant 600 according to some embodiments of the present disclosure are provided. In the illustrated embodiments, a flange portion 670 is included in socket portion 640 to limit the rotation of the ball portion 620 relative to socket portion 640 in the plantar flexion direction. As shown in FIGS. 6E and 6F, ball portion 620 can be disposed asymmetrically relative to socket portion 640 to further limit the rotation of the ball portion 620 relative to socket portion 640 in the plantar flexion direction. As shown in the illustrated embodiment, ball portion 620 and socket portion 640 include respective spherical articulating surfaces which provide rotation of the ball portion 620 a predetermined amount relative to the socket portion 640.

Figure 6G:
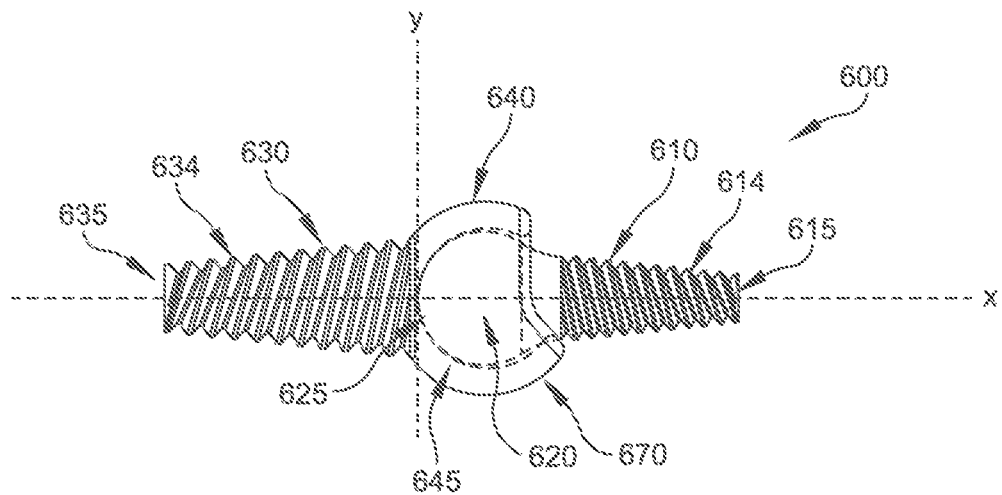
FIG. 6G is a side elevational view, partially in phantom, of a hammertoe implant shown in FIGS. 6A-6F, showing threaded portions.
Figure 6H:
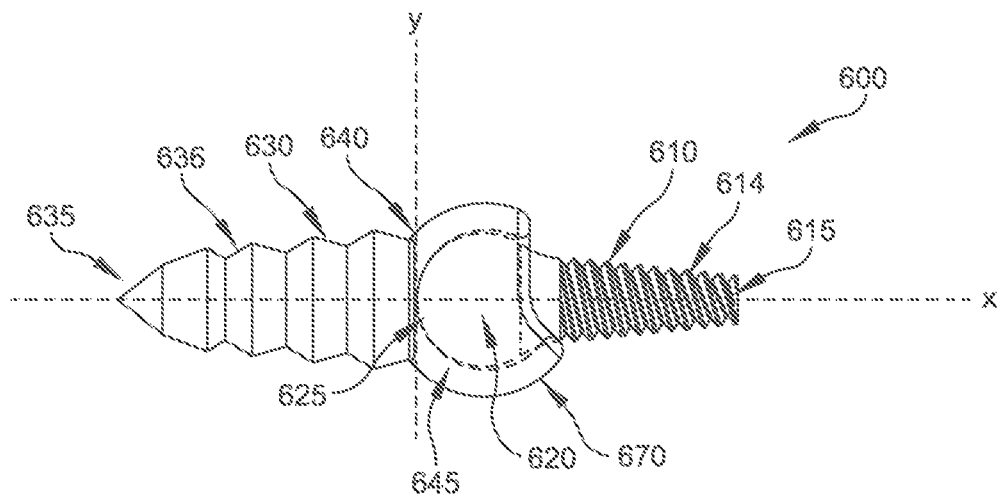
FIG. 6H is a side elevational view, partially in phantom, of the hammertoe implant of FIGS. 6A-6F but including a threaded portion and a blade portion.

As shown in FIG. 6G, in embodiments where the implant 600 is assembled in situ, first portion 630 and second portion 610 can include respective threaded portion 634, 614. In embodiments where the implant 600 in assembled prior to insertion into the joint (at block 720), one of the first 630 or second 610 portions can include a respective threaded portion (e.g. FIG. 6H and threaded portion 614) and the other one of the first 630 or second 610 portions of the implant 600 can include a bladed portion (e.g. FIG. 6H and threaded portion 616). In some embodiments, the other one of the first 630 or second 610 portions of the implant 600 can include a barbed portion (not shown). In some embodiments (not shown), implant 600 can include a resorbable portion operatively connected to the first 630 and second 610 portions and configured to limit the rotation of the ball portion 620 respective to the socket portion 640 for a predetermined period of time as described above. In embodiments having a resorbable portion, a barbed or bladed portion can be included on the portion of the implant 600 configured for insertion into the distal bone for improved alignment and implantation.

Figure 8:
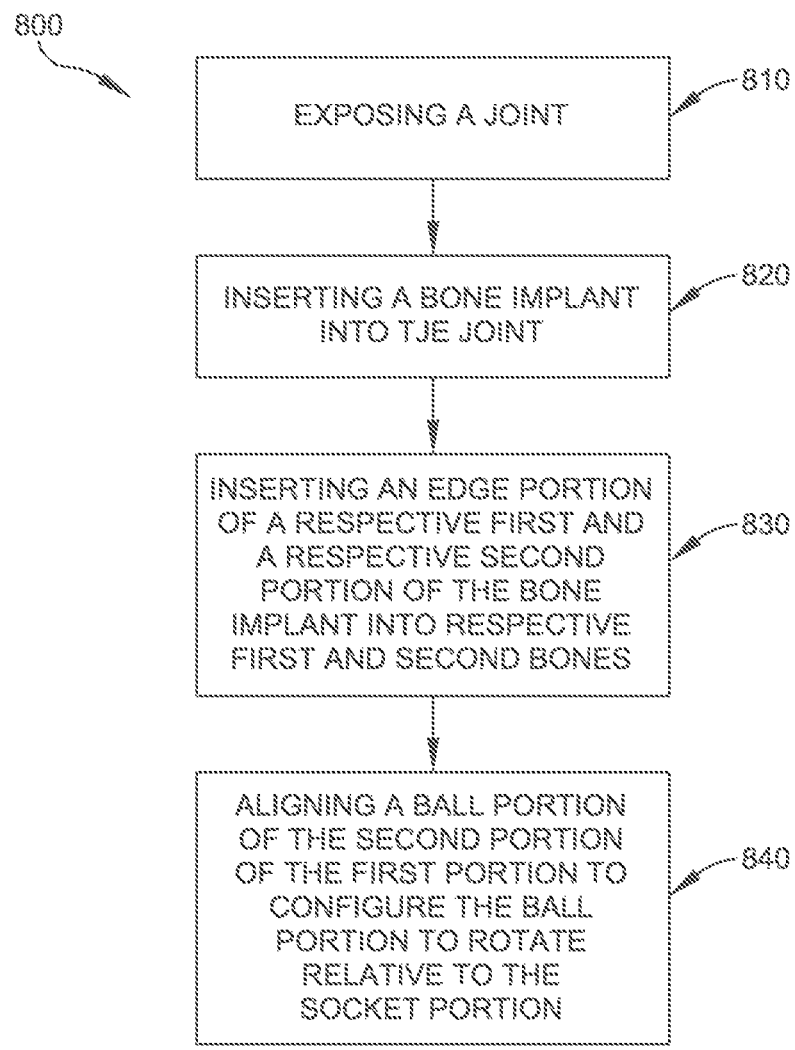
FIG. 8 is a further flow chart illustrating a method for correcting a bone joint according to one embodiment of the invention.

Referring now to FIG. 8, a a flow chart showing a method of correcting a toe bone deformity is provided. At block 810, a joint is exposed between first and second bones as described above for block 710. In some embodiments, the joint is a proximal interphalangeal (PIP) joint. In some embodiments, the joint is a distal interphalangeal (DIP) joint. In some embodiments, the joint is a metatarsal phalangeal joint. At block 820, bone implant 100 (200, 300, 400, 500, 600) can be inserted into the joint as described above for block 720. At block 830, an edge portion of the respective first 130 (230, 330, 430, 530, 630) and second 110 (210, 310, 410, 510, 610) portions is inserted into the respective first and second bones as described above for block 730. At block 840, a ball portion 120 (220, 320, 420, 520, 620) of the second portion 110 (210, 310, 410, 510, 610) can be aligned with a socket portion 140 (240, 340, 440, 540, 640) of the first portion 130 (230, 330, 430, 530, 630) such that the ball portion 120 (220, 320, 420, 520, 620) is configured to rotate a predetermined amount relative to the socket portion 140 (240, 340, 440, 540, 640) In some embodiments, a ball portion 220 (320, 420, 620) of second portion 210 (310, 410, 610) can be operatively connected to a socket portion 240 (340, 440, 640) of first portion 230 (330, 430, 630) in situ. In some embodiments, a ball portion 120 (520, 620) of second portion 110 (510, 610) can be operatively connected to a socket portion 140 (540, 640) of first portion 130 (530, 630) prior to inserting the bone implant 100 (500, 600) into a joint (820). In some embodiments, the respective edge portions of ball portion 120 (220, 320, 420, 520, 620) of second portion 110 (210, 310, 410, 510, 610) and socket portion 140 (240, 340, 440, 540, 640) of first portion 130 (230, 330, 430, 530, 630) are inserted into respective first and second bones such that the ball portion 120 (220, 320, 420, 520, 620) is aligned with socket portion 140 (240, 340, 440, 540, 640) and is configured to rotate a predetermined amount relative to the socket portion 140 (240, 340, 440, 540, 640).

Although reference has been made to a patient's proximal and distal interphalangeal joints and metatarsal phalangeal joints, one skilled in the art will understand that embodiments of the present disclosure may be implemented for other respective bones including, but not limited to other phalanges/digits and phalangeal/digital joints.

It may be emphasized that the above-described and illustrated embodiments are merely possible examples of implementations and merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claims.

While this specification contains many specifics, these should not be construed as limitations on the scope of the claimed subject matter, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

As shown by the various configurations and embodiments illustrated in FIGS. 1A-8, improved toe bone implants and methods of correcting toe bone deformities have been described.

Some embodiments provide a toe bone implant. The toe bone implant includes a first portion having a socket portion. The toe bone implant also includes a second portion having a ball portion operatively connected to the socket portion. The toe bone implant is implanted in a joint such that the ball portion is configured to rotate a predetermined amount respective to the socket portion.

Some embodiments provide a method of correcting a toe bone deformity. The method includes exposing a joint between first and second bones and inserting a bone implant into the joint. The bone implant includes a first portion including a socket portion and a second portion including a ball portion operatively connected to the socket portion. The method includes inserting an edge portion of the respective first and second portions into the respective first and second bones, and aligning the ball portion with the socket portion such that the ball portion is configured to rotate a predetermined amount relative to the socket portion.

Some embodiments provide a toe bone implant. The toe bone implant includes a first portion having a socket portion. The toe bone implant includes a second portion having a ball portion operatively connected to the socket portion such that the ball portion is configured to rotate a predetermined amount respective to the socket portion. The toe bone implant also includes a resorbable portion operatively connected to the first and second portions and configured to limit rotation of the ball portion respective to the socket portion for a predetermined period of time.

While various embodiments are described herein, it is to be understood that the embodiments described are illustrative only and that the scope of the subject matter is to be accorded a full range of equivalents, many variations and modifications naturally occurring to those of skill in the art from a perusal hereof.

We claim:

1. A toe bone implant, comprising:
   a first portion comprising a socket portion;
   a second portion comprising a ball portion operatively connected to the socket portion; and a resorbable portion operatively connected to the first and second portions and configured to limit rotation of the ball portion respective to the socket portion for a predetermined period of time of approximately 8 to 12 weeks and when the implant is implanted in a joint.

2. The bone implant of claim 1, wherein the resorbable portion is selected from the group consisting of a resorbable pin, a resorbable bridge, a resorbable lock out device, and a resorbable snap-on device.

3. The bone implant of claim 1, wherein the ball portion is configured to rotate a predetermined amount in a longitudinal direction.

4. The bone implant of claim 1, wherein the ball portion is configured to rotate a predetermined amount in a lateral direction.

5. The bone implant of claim 1, wherein the ball portion is configured to freely rotate about an axis of rotation.

6. The bone implant of claim 1, wherein the joint is a proximal interphalangeal (PIP) joint.

7. The bone implant of claim 1, wherein the joint is a metatarsal phalangeal joint.

8. The bone implant of claim 1, wherein one or more of the first or second portions comprises a threaded edge portion.

9. The bone implant of claim 1, wherein one or more of the first or second portions comprises an edge portion comprising blades.

10. A toe bone implant, comprising:
    a first portion comprising a socket portion;
    a second portion comprising a ball portion operatively connected to the socket portion such that the ball portion is configured to rotate a predetermined amount respective to the socket portion; and
    a resorbable portion operatively connected to the first and second portions and configured to limit rotation of the ball portion respective to the socket portion for a predetermined period of time.

11. The bone implant of claim 10, wherein the ball portion is configured to rotate a predetermined amount in a longitudinal direction.

12. The bone implant of claim 10, wherein the ball portion is configured to rotate a predetermined amount in a lateral direction.

13. The bone implant of claim 10, wherein the ball portion is configured to freely rotate about an axis of rotation.

14. The bone implant of claim 10, wherein the joint is a proximal interphalangeal (PIP) joint.

15. The bone implant of claim 10, wherein the joint is a metatarsal phalangeal joint.

16. The bone implant of claim 10, wherein one or more of the first or second portions comprises a threaded edge portion.

17. The bone implant of claim 10, wherein one or more of the first or second portions comprises an edge portion comprising blades.

18. A toe bone implant, comprising:
    a first portion comprising a socket portion;
    a second portion comprising a ball portion operatively connected to the socket portion such that the ball portion is configured to rotate a predetermined amount respective to the socket portion; and
    a resorbable portion selected from the group consisting of a resorbable pin, a resorbable bridge, a resorbable lock out device, and a resorbable snap-on device is operatively connected to the first and second portions and configured to limit rotation of the ball portion respective to the socket portion for a predetermined period of time.

* * * * *